(12) United States Patent
Montgomery et al.

(10) Patent No.: US 7,651,528 B2
(45) Date of Patent: Jan. 26, 2010

(54) DEVICES, SYSTEMS AND METHODS FOR MATERIAL FIXATION

(75) Inventors: Kenneth D. Montgomery, Roslyn, NY (US); Sidney D. Fleischman, Durham, NC (US); James G. Whayne, Chapel Hill, NC (US); Kevin L. Ohashi, Jamaica Plain, MA (US); Nicanor Domingo, Santa Clara, CA (US); John Wright, Kearney, NE (US); Derek J. Harper, Goleta, CA (US); Heber Crockett, Kearney, NE (US)

(73) Assignee: Cayenne Medical, Inc., Scottsdale, AZ (US)

( * ) Notice: Subject to any disclaimer, the term of this patent is extended or adjusted under 35 U.S.C. 154(b) by 84 days.

(21) Appl. No.: 11/281,566

(22) Filed: Nov. 18, 2005

(65) Prior Publication Data

US 2006/0155287 A1    Jul. 13, 2006

Related U.S. Application Data

(60) Provisional application No. 60/628,774, filed on Nov. 18, 2004, provisional application No. 60/671,510, filed on Apr. 15, 2005.

(51) Int. Cl.
*A61F 2/08* (2006.01)
(52) U.S. Cl. .................................... 623/13.14
(58) Field of Classification Search ............ 606/72, 606/232, 60, 224, 225, 215, 216, 313, 90, 606/237; 623/13.11, 13.12, 13.13, 13.14; 411/517
See application file for complete search history.

(56) References Cited

U.S. PATENT DOCUMENTS

| 3,708,883 A | 1/1973 | Flander |
| 3,832,931 A | 9/1974 | Talan |

(Continued)

FOREIGN PATENT DOCUMENTS

CA    2235354 A1    10/1999

(Continued)

OTHER PUBLICATIONS

International Search Report, Jul. 18, 2006, for PCT/US2005/041924.

(Continued)

*Primary Examiner*—Pedro Philogene
(74) *Attorney, Agent, or Firm*—Stout, Uxa, Buyan & Mullins, LLP

(57) ABSTRACT

Devices, systems and methods for fixation of tendon to bone are described. An exemplary surgical implant is a modified bone anchor that is able to grasp the tendon and hold it firmly in a bone tunnel. Once deployed, the anchor delivers lateral compression to the tendon, providing direct tendon to bone compression to facilitate healing. The anchor has different versions which allow it to be attached to the tendon prior to insertion into the bone tunnel, or be inserted between tendon arms when the surgical procedure dictates. The resulting tendon to bone compression allows for the firm fixation in a manner markedly simpler than traditional techniques. A modification of this anchor can also allow the anchor to grasp and hold suture. This variation facilitates the technique for knotless rotator cuff repair.

18 Claims, 50 Drawing Sheets

U.S. PATENT DOCUMENTS

| | | | |
|---|---|---|---|
| 4,311,421 A | 1/1982 | Okada et al. | |
| 4,711,232 A | 12/1987 | Fischer et al. | |
| 4,716,893 A | 1/1988 | Fischer et al. | |
| 4,738,255 A | 4/1988 | Goble et al. | |
| 4,744,793 A | 5/1988 | Parr et al. | |
| 4,772,286 A | 9/1988 | Goble et al. | |
| 4,778,468 A | 10/1988 | Hunt et al. | |
| 4,828,562 A | 5/1989 | Kenna | |
| 4,955,910 A | 9/1990 | Bolesky | |
| 5,004,474 A | 4/1991 | Fronk et al. | |
| 5,037,422 A | 8/1991 | Hayhurst et al. | |
| 5,139,520 A | 8/1992 | Rosenberg | |
| 5,176,709 A | 1/1993 | Branemark | |
| 5,211,647 A | 5/1993 | Schmieding | |
| 5,234,430 A | 8/1993 | Huebner | |
| 5,236,445 A | 8/1993 | Hayhurst et al. | |
| 5,258,016 A | 11/1993 | DiPoto et al. | |
| 5,268,001 A | 12/1993 | Nicholson et al. | |
| 5,336,240 A | 8/1994 | Metzler et al. | |
| 5,354,298 A | 10/1994 | Lee et al. | |
| 5,356,435 A | 10/1994 | Thein | |
| 5,374,269 A | 12/1994 | Rosenberg | |
| 5,383,878 A | 1/1995 | Roger et al. | |
| 5,411,523 A | 5/1995 | Goble | |
| 5,431,651 A | 7/1995 | Goble | |
| 5,456,685 A | 10/1995 | Huebner | |
| 5,464,427 A * | 11/1995 | Curtis et al. | 606/232 |
| 5,466,237 A | 11/1995 | Byrd et al. | |
| 5,474,555 A | 12/1995 | Puno et al. | |
| 5,480,403 A * | 1/1996 | Lee et al. | 606/72 |
| 5,486,197 A * | 1/1996 | Le et al. | 606/232 |
| 5,571,104 A | 11/1996 | Li | |
| 5,571,184 A | 11/1996 | DeSatnick | |
| 5,575,819 A | 11/1996 | Amis | |
| 5,601,562 A | 2/1997 | Wolf et al. | |
| 5,603,716 A | 2/1997 | Morgan et al. | |
| 5,618,314 A | 4/1997 | Harwin et al. | |
| 5,632,748 A | 5/1997 | Beck, Jr. et al. | |
| 5,645,589 A | 7/1997 | Li | |
| 5,702,215 A * | 12/1997 | Li | 411/21 |
| 5,702,397 A | 12/1997 | Goble et al. | |
| 5,707,395 A | 1/1998 | Li | |
| 5,713,903 A | 2/1998 | Sander et al. | |
| 5,718,706 A | 2/1998 | Roger | |
| 5,725,529 A | 3/1998 | Nicholson et al. | |
| 5,725,541 A | 3/1998 | Anspach, III et al. | |
| 5,728,136 A | 3/1998 | Thal | |
| 5,741,300 A | 4/1998 | Li | |
| 5,743,912 A | 4/1998 | Lahille et al. | |
| 5,769,894 A | 6/1998 | Ferragamo | |
| 5,782,865 A | 7/1998 | Grotz | |
| 5,814,073 A | 9/1998 | Bonutti | |
| 5,845,645 A | 12/1998 | Bonutti | |
| 5,871,504 A | 2/1999 | Eaton et al. | |
| 5,899,938 A | 5/1999 | Sklar et al. | |
| 5,902,303 A | 5/1999 | Eckhoff et al. | |
| 5,911,721 A | 6/1999 | Nicholson et al. | |
| RE36,286 E | 8/1999 | Le et al. | |
| RE36,289 E | 8/1999 | Le et al. | |
| 5,931,869 A | 8/1999 | Boucher et al. | |
| 5,935,129 A * | 8/1999 | McDevitt et al. | 606/72 |
| 5,941,901 A | 8/1999 | Egan | |
| 5,957,953 A | 9/1999 | DiPoto et al. | |
| 5,961,520 A | 10/1999 | Beck, Jr. et al. | |
| 5,964,764 A | 10/1999 | West, Jr. et al. | |
| 5,968,078 A | 10/1999 | Grotz | |
| 5,993,459 A | 11/1999 | Larsen et al. | |
| 6,017,346 A | 1/2000 | Grotz | |
| 6,086,608 A | 7/2000 | Ek et al. | |
| 6,099,530 A | 8/2000 | Simonian et al. | |
| 6,113,609 A * | 9/2000 | Adams | 606/139 |
| 6,117,173 A | 9/2000 | Taddia et al. | |
| 6,132,433 A | 10/2000 | Whelan | |
| 6,146,406 A | 11/2000 | Shluzas et al. | |
| 6,152,928 A | 11/2000 | Wenstrom, Jr. | |
| 6,179,840 B1 * | 1/2001 | Bowman | 606/72 |
| 6,187,008 B1 | 2/2001 | Hamman | |
| 6,190,411 B1 | 2/2001 | Lo | |
| 6,214,007 B1 | 4/2001 | Anderson | |
| 6,221,107 B1 | 4/2001 | Steiner et al. | |
| 6,325,804 B1 | 12/2001 | Wenstrom, Jr. et al. | |
| 6,328,758 B1 | 12/2001 | Tornier et al. | |
| 6,355,066 B1 | 3/2002 | Kim | |
| 6,379,361 B1 | 4/2002 | Beck, Jr. et al. | |
| 6,387,129 B2 | 5/2002 | Rieser et al. | |
| 6,461,373 B2 | 10/2002 | Wyman et al. | |
| 6,482,210 B1 | 11/2002 | Skiba et al. | |
| 6,517,579 B1 | 2/2003 | Paulos et al. | |
| 6,533,816 B2 | 3/2003 | Sklar | |
| 6,554,862 B2 | 4/2003 | Hays et al. | |
| 6,562,071 B2 | 5/2003 | Jarvinen | |
| 6,616,694 B1 | 9/2003 | Hart | |
| 6,623,524 B2 | 9/2003 | Schmieding | |
| 6,632,245 B2 | 10/2003 | Kim | |
| 6,648,890 B2 | 11/2003 | Culbert et al. | |
| 6,656,183 B2 * | 12/2003 | Colleran et al. | 606/72 |
| 6,685,706 B2 * | 2/2004 | Padget et al. | 606/309 |
| 6,736,829 B1 | 5/2004 | Li et al. | |
| 6,736,847 B2 | 5/2004 | Seyr et al. | |
| 6,752,831 B2 | 6/2004 | Sybert et al. | |
| 6,770,073 B2 | 8/2004 | McDevitt et al. | |
| 6,780,188 B2 | 8/2004 | Clark et al. | |
| 6,796,977 B2 | 9/2004 | Yap et al. | |
| 6,802,862 B1 | 10/2004 | Roger et al. | |
| 6,833,005 B1 | 12/2004 | Mantas et al. | |
| 6,887,271 B2 | 5/2005 | Justin et al. | |
| 6,890,354 B2 | 5/2005 | Steiner et al. | |
| 6,932,841 B2 | 8/2005 | Sklar et al. | |
| 6,939,379 B2 | 9/2005 | Sklar | |
| 6,942,666 B2 | 9/2005 | Overaker et al. | |
| 6,942,668 B2 | 9/2005 | Padget et al. | |
| 6,986,781 B2 * | 1/2006 | Smith | 606/232 |
| 7,008,451 B2 | 3/2006 | Justin et al. | |
| 7,037,324 B2 * | 5/2006 | Martinek | 606/232 |
| 7,083,638 B2 * | 8/2006 | Foerster | 606/232 |
| 7,201,754 B2 * | 4/2007 | Stewart et al. | 606/72 |
| 7,309,355 B2 | 12/2007 | Donnelly et al. | |
| 7,326,247 B2 | 2/2008 | Schmieding et al. | |
| 7,556,629 B2 | 7/2009 | Von Hoffmann et al. | |
| 7,556,640 B2 | 7/2009 | Foerster | |
| 2003/0065391 A1 | 4/2003 | Re et al. | |
| 2003/0083662 A1 | 5/2003 | Middleton | |
| 2003/0109900 A1 | 6/2003 | Martinek | |
| 2003/0135274 A1 | 7/2003 | Hays et al. | |
| 2003/0199877 A1 | 10/2003 | Steiger et al. | |
| 2003/0204204 A1 * | 10/2003 | Bonutti | 606/232 |
| 2004/0024456 A1 | 2/2004 | Brown, Jr. et al. | |
| 2004/0097943 A1 | 5/2004 | Hart | |
| 2004/0098052 A1 | 5/2004 | West, Jr. et al. | |
| 2004/0153153 A1 | 8/2004 | Elson et al. | |
| 2004/0180308 A1 | 9/2004 | Ebi et al. | |
| 2004/0181240 A1 | 9/2004 | Tseng et al. | |
| 2004/0199165 A1 | 10/2004 | Culbert et al. | |
| 2004/0230194 A1 | 11/2004 | Urbanski et al. | |
| 2004/0267362 A1 | 12/2004 | Hwang et al. | |
| 2005/0033289 A1 | 2/2005 | Warren et al. | |
| 2005/0251260 A1 | 11/2005 | Gerber et al. | |
| 2006/0095131 A1 | 5/2006 | Justin et al. | |
| 2006/0155287 A1 | 7/2006 | Montgomery et al. | |

FOREIGN PATENT DOCUMENTS

| | | |
|---|---|---|
| EP | 0232049 B1 | 3/1990 |
| EP | 0528573 A1 | 8/1992 |

| | | | | | | | |
|---|---|---|---|---|---|---|---|
| EP | 0688185 | A1 | 2/1993 | WO | WO9812991 | A1 | 4/1998 |
| EP | 1033115 | A2 | 9/2000 | WO | WO9818409 | | 5/1998 |
| EP | 0762850 | B1 | 2/2004 | WO | WO0130253 | A1 | 5/2001 |
| EP | 0739185 | B1 | 9/2004 | WO | WO02085256 | A1 | 10/2002 |
| EP | 1011535 | B1 | 12/2005 | | | | |
| FR | 2696925 | A1 | 4/1994 | | | | |
| JP | 10155820 | A | 6/1998 | | | | |
| WO | WO8809157 | | 12/1988 | | | | |
| WO | WO9216167 | A1 | 10/1992 | | | | |
| WO | WO9515726 | A1 | 6/1995 | | | | |

OTHER PUBLICATIONS

Written Opinion, Jul. 18, 2006, for PCT/US2005/041924.

* cited by examiner

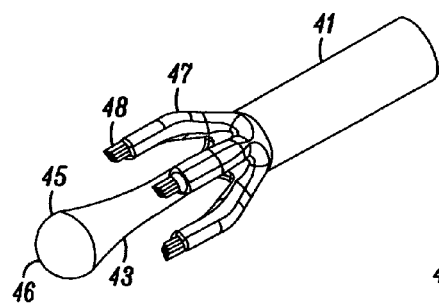
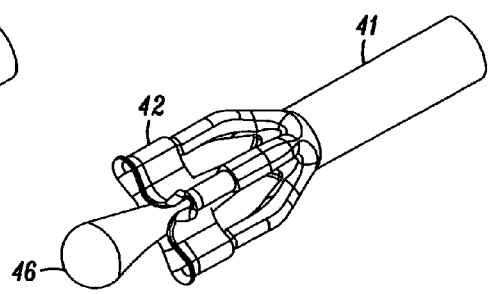
FIG. 4A              FIG. 4B
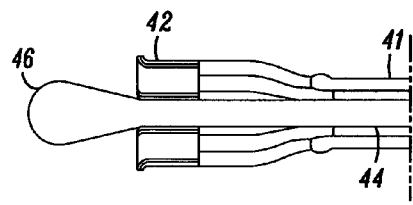
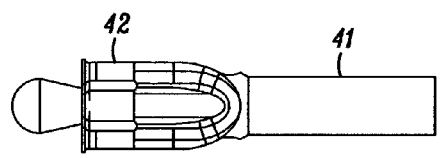
FIG. 4C              FIG. 4D
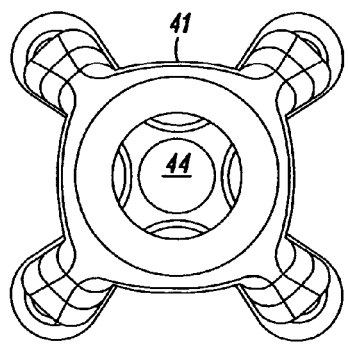
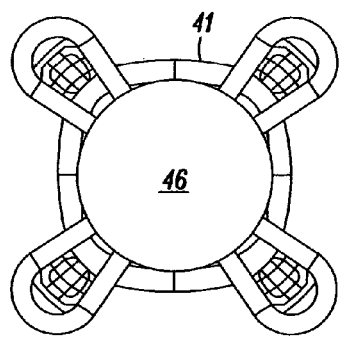
FIG. 4E              FIG. 4F

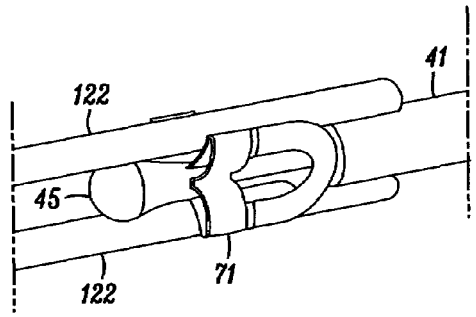
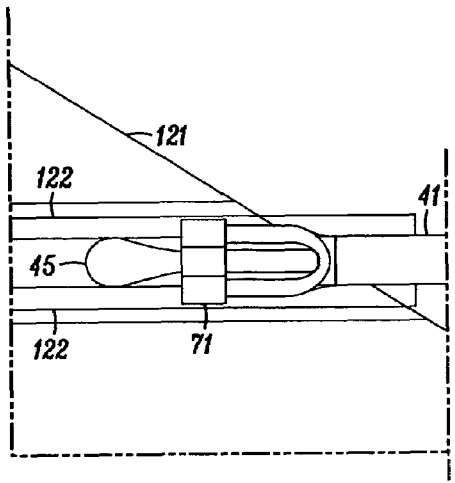
FIG. 12A  FIG. 12B
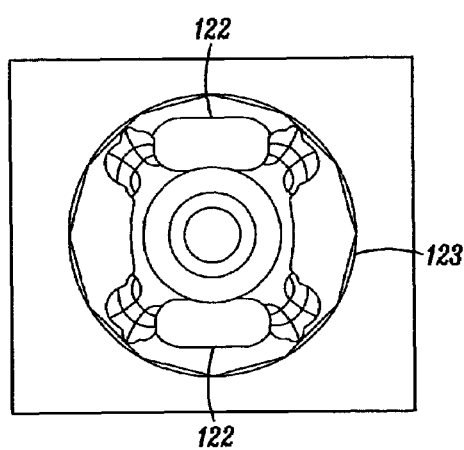
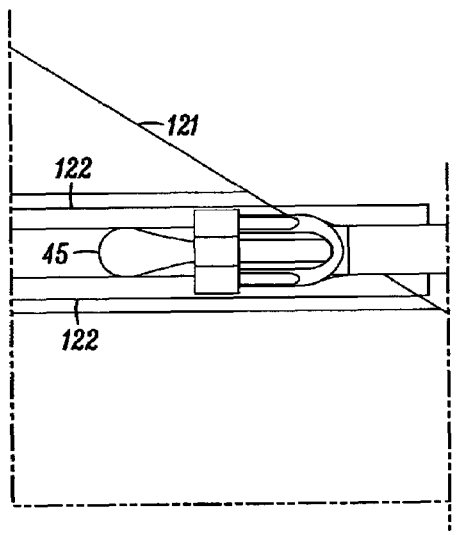
FIG. 12C  FIG. 12D

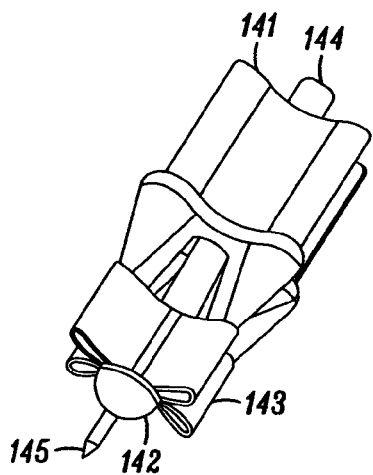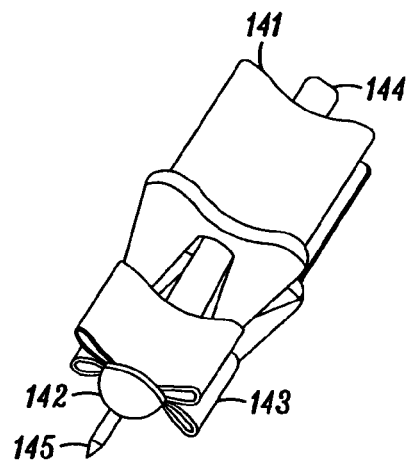
FIG. 14A    FIG. 14B
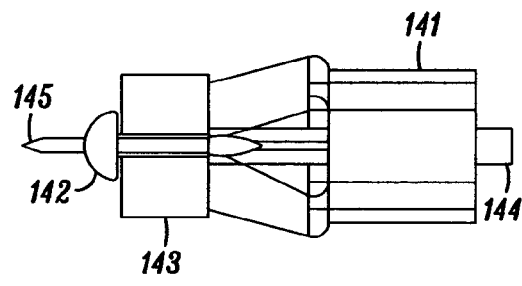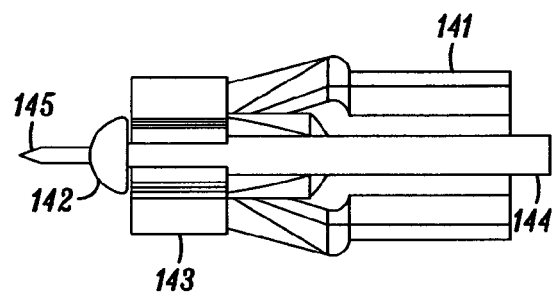
FIG. 14C    FIG. 14D

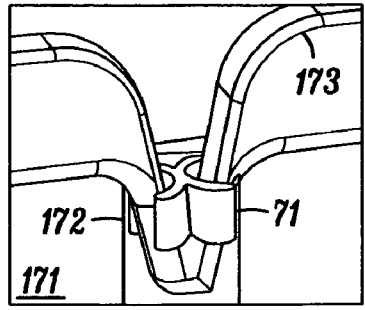 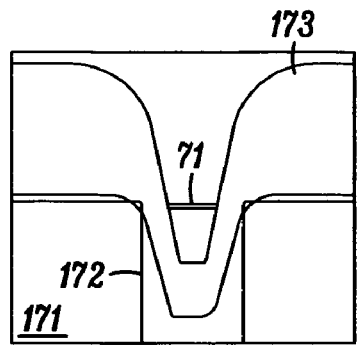
*FIG. 17A*  *FIG. 17B*
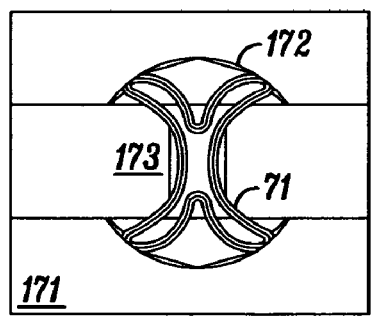
*FIG. 17C*

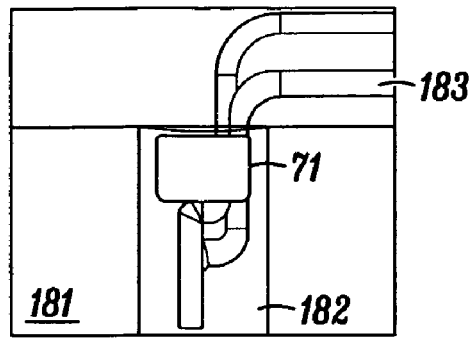
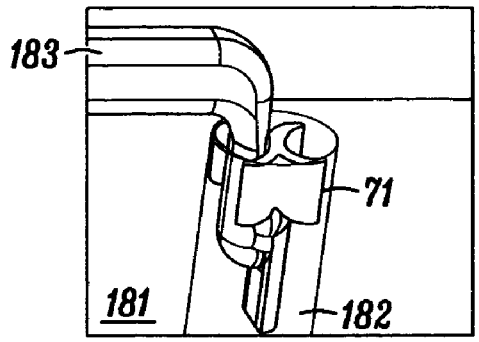
*FIG. 18A*  *FIG. 18B*
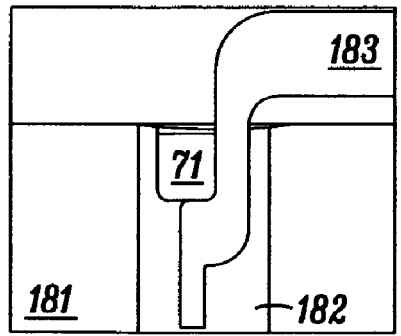
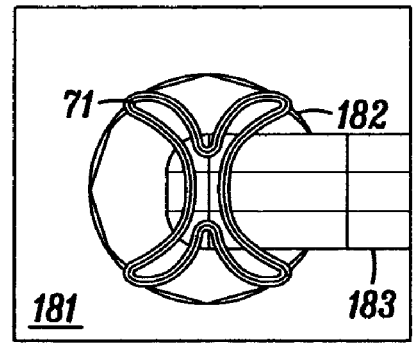
*FIG. 18C*  *FIG. 18D*

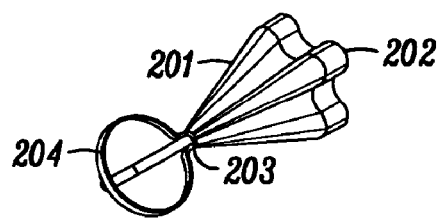
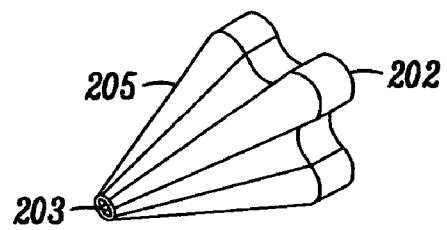
FIG. 20A    FIG. 20B
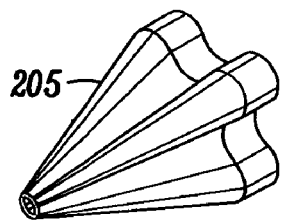
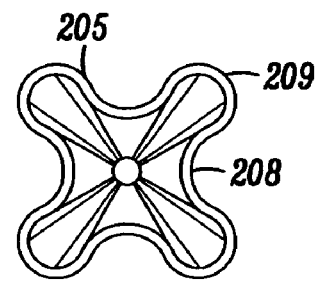
FIG. 20C    FIG. 20D
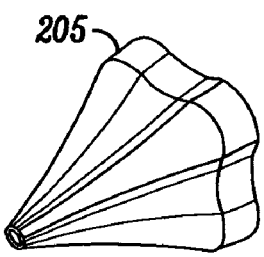
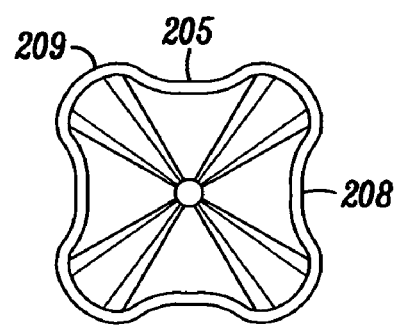
FIG. 20E    FIG. 20F

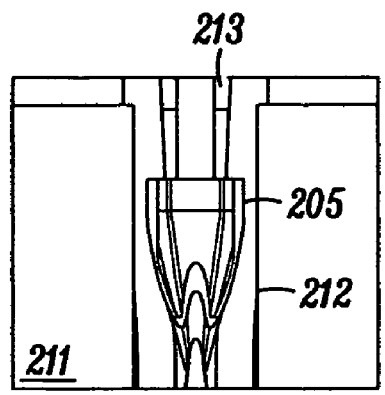
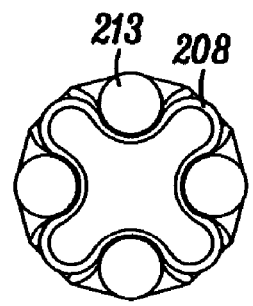
*FIG. 21A*      *FIG. 21B*
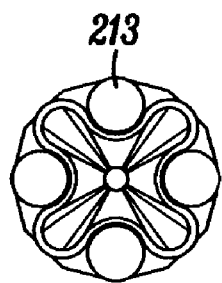
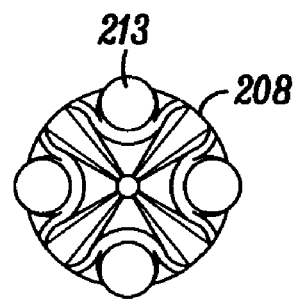
*FIG. 21C*      *FIG. 21D*

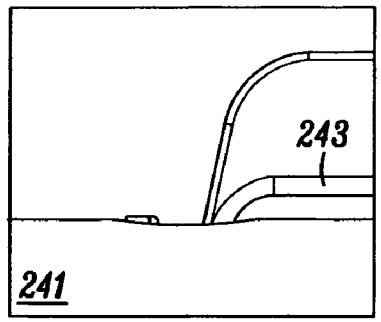
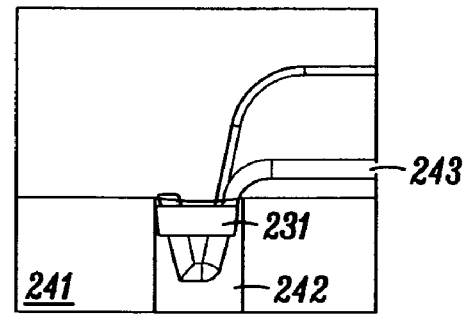
FIG. 24A     FIG. 24B
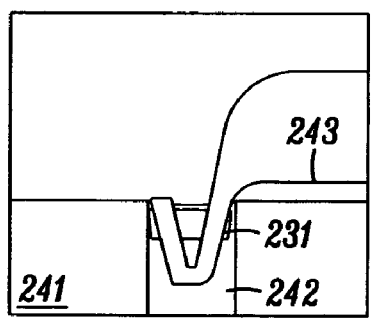
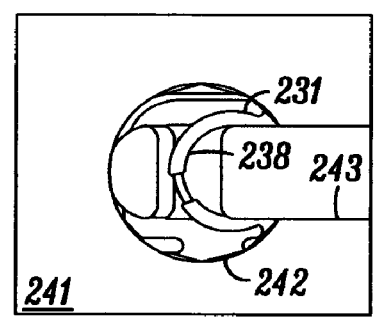
FIG. 24C     FIG. 24D

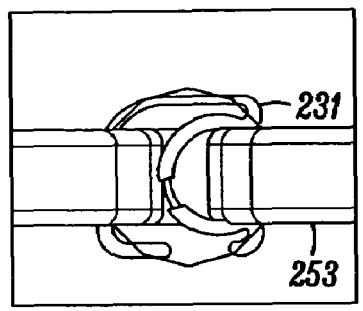
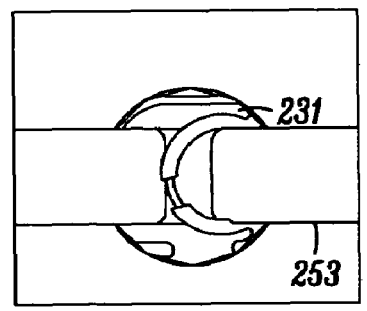
*FIG. 25A*  *FIG. 25B*
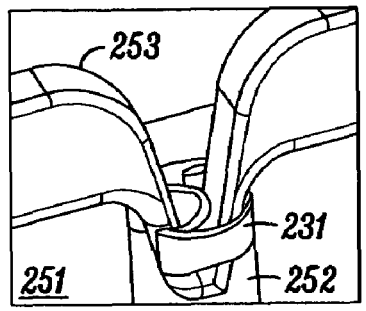
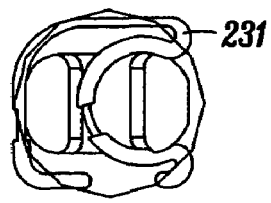
*FIG. 25C*  *FIG. 25D*
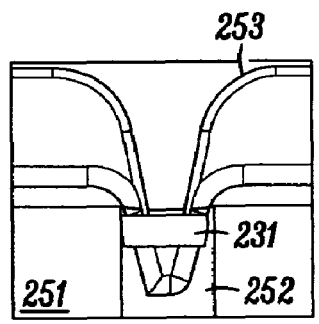
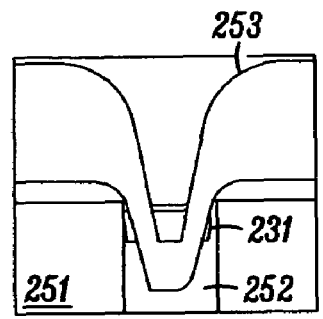
*FIG. 25E*  *FIG. 25F*

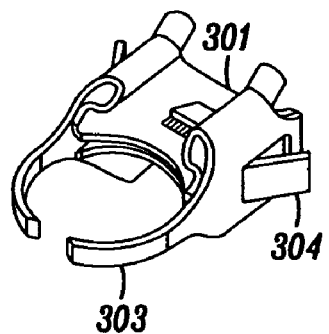
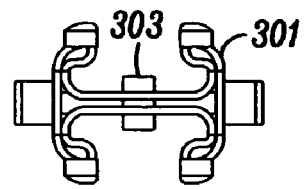
*FIG. 30A*  *FIG. 30B*
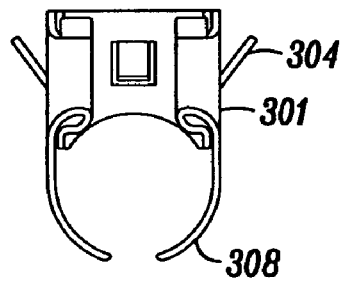
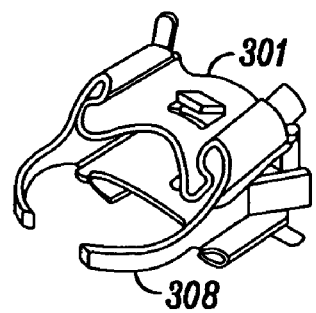
*FIG. 30C*  *FIG. 30D*
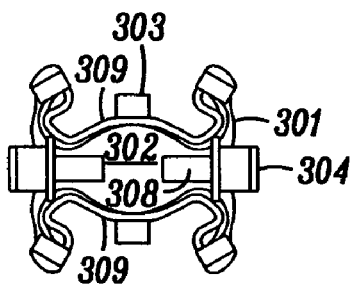
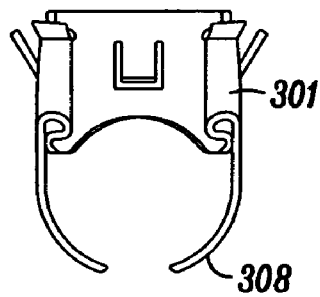
*FIG. 30E*  *FIG. 30F*

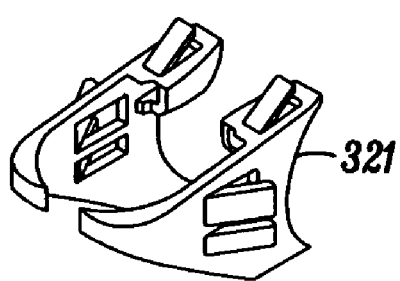
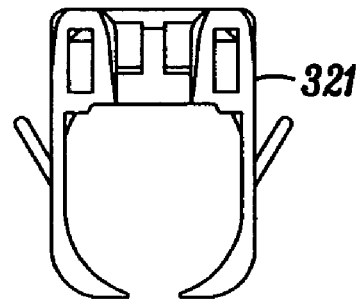
FIG. 32A
FIG. 32B
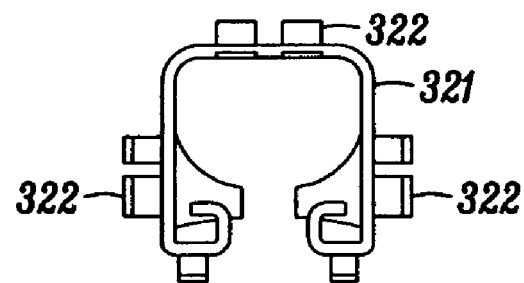
FIG. 32C

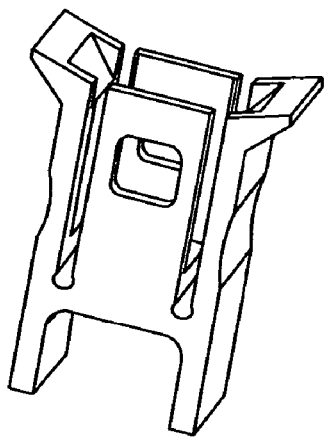 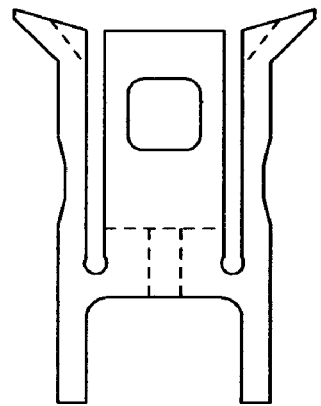
FIG. 42A          FIG. 42B
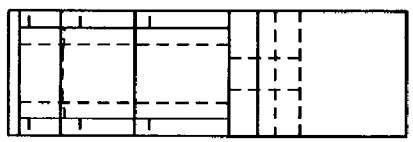 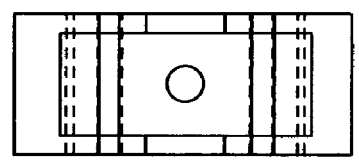
FIG. 42C          FIG. 42D

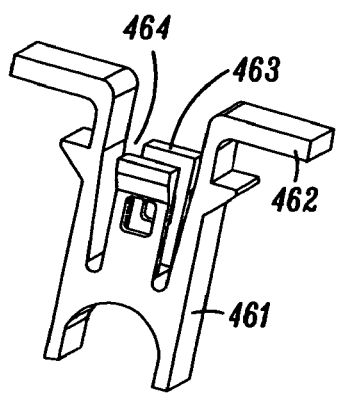
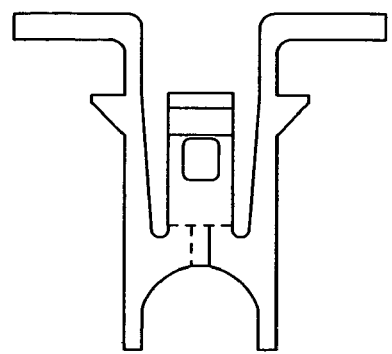
FIG. 46A                FIG. 46B
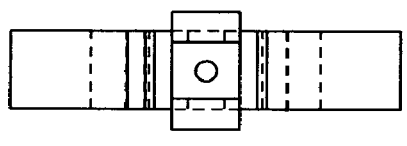
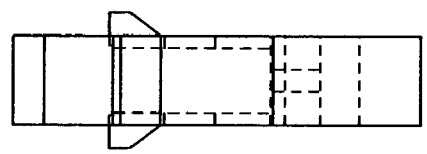
FIG. 46C                FIG. 46D

DEVICES, SYSTEMS AND METHODS FOR MATERIAL FIXATION

This U.S. Utility Patent Application claims priority to U.S. Provisional Patent Application Ser. No. 60/628,774, filed Nov. 18, 2004, and U.S. Provisional Patent Application Ser. No. 60/671,510, filed Apr. 15, 2005, the contents of each of which are hereby incorporated by reference in their entirety into this disclosure.

BACKGROUND OF THE INVENTION

1. Field of the Invention

The present invention relates generally to devices, systems and methods for material fixation. More specifically, the present invention relates to a technique that can be used to firmly hold a soft tissue or graft against bone tissue within a bone tunnel.

2. Background of the Invention

One of the most common needs in orthopedic surgery is the fixation of tendon to bone. The fixation of diseased tendons into a modified position is called tenodesis and is commonly required in patients with injury to the long head of the biceps tendon in the shoulder. In addition, tendons which are torn from their insertion site into bone also frequently require repair. This includes distal biceps tendon tears, rotator cuff tears, and torn flexor tendons in the hand. Tendons are also frequently used in the reconstruction of unstable joints. Common examples include anterior cruciate ligament and collateral ligament reconstructions of the knee, medial and lateral elbow collateral ligament reconstructions, ankle collateral ligament reconstruction, finger and hand collateral ligament reconstructions and the like.

Traditional techniques that are used to fix tendon to bone suffer from a number of limitations as a result of the methodology used, including the use of a "keyhole" tenodesis, pull-out sutures, bone tunnels, and interference screw fixation. The "keyhole" tenodesis requires the creation of a bone tunnel in the shape of a keyhole, which allows a knotted tendon to be inserted into the upper portion, and subsequently wedged into the lower narrower portion of the tunnel where inherent traction on the tendon holds it in place. This technique is challenging as it is often difficult to sculpt the keyhole site and insert the tendon into the tunnel. In addition, if the tendon knot unravels in the postoperative period, the tendon will slide out of the keyhole, losing fixation.

Another traditional form of tendon fixation is the use of the "pull-out stitch." With this technique, sutures attached to the tendon end are passed through bone tunnels and tied over a post or button on the opposite side of the joint. This technique has lost favor in recent years due to a host of associated complications, which include wound problems, weak fixation strength, and potential injury to adjacent structures.

The most common method of fixation of tendon to bone is the use of bone tunnels with either suture fixation, or interference screw fixation. The creation of bone tunnels is relatively complicated, often requiring an extensive exposure to identify the margins of the tunnels. Drill holes placed at right angles are connected using small curettes. This tedious process is time-consuming and fraught with complications, which include poor tunnel placement and fracture of the overlying bone bridge. Graft isometry, which is easy to determine with single point fixation, is difficult to achieve because the tendon exits the bone from two points. After creation of tunnels, sutures must be passed through the tunnels to facilitate the passage of the tendon graft. Tunnels should be small enough to allow good tendon-bone contact, yet large enough to allow for graft passage without compromising the tendon. This portion of the procedure is often time-consuming and frustrating to a surgeon. Finally, the procedure can be compromised if the bone bridge above the tunnel breaks, resulting in loss of fixation. The technique restricts fixation to the strength of the sutures, and does not provide any direct tendon to bone compression.

More recent advances in the field of tendon fixation involve the use of an internally deployed toggle button, for example, the ENDOBUTTON, and the use of interference screws to provide fixation. The ENDOBUTTON allows the fixation of tendon into a bone tunnel by creating an internally deployed post against a bony wall. While this technique eliminates the need for secondary incisions to place the post, the fixation strength is limited to suture strength alone. This technique does not provide direct tendon to bone compression; as such this technique may slow healing and lead to graft tunnel widening due to the "bungee effect" and "windshield wiper effect". As a result, this technique has limited clinical applications and is used primarily for salvage when bone tunnels break or backup fixation is important.

The use of the interference screw is the most notable advance in the fixation of tendon to bone. The screw is inserted adjacent to a tendon in a bone tunnel, providing axial compression between the screw threads and the bony wall. Advantages include acceptable pull-out strength and relative ease of use. Aperture fixation, the ability to fix the tendon to bone at its entrance site, is a valuable adjunct to this technique as it minimizes graft motion and subsequent tunnel widening. Some disadvantages related to soft tissue interference screws are that they can be difficult to use, and can also cut or compromise the tendon during implantation.

The newest generation interference screw allows the ability to provide tendon to bone fixation with limited exposure. For example, the BIO-TENODESIS SCREW (Arthrex, Inc.) allows the tensioning and insertion of tendon into bone, followed by insertion of an adjacent soft tissue interference screw. While this screw system provides advantages in the insertion of tendon into bone in cases when a pull through stitch is not available, it is still limited by the potential for tendon rotation or disruption as the screw compresses the tendon. The surgical technique is also complicated, typically requiring two or more hands for insertion, making it difficult to use the system without assistance during arthroscopic or open procedures. Finally, the use of the screw requires preparation of the tendon end, which can be difficult, time consuming, and can also require conversion of an arthroscopic procedure to open.

Thus, although there are many conventional techniques used for the fixation of tendon to bone, each having some advantages, the disadvantages of each such technique presents a need in the art for a simple and universal technique to fixate tendon to bone such that the device is easy to use, the process is simple to follow, and the result is a firm and secure tendon to bone fixation with minimal negative effect on the tendon. Further, such device should be easy to manufacture, universally applied to different tendon to bone sites, and require minimal effort to understand and use in practice.

SUMMARY OF THE INVENTION

The present invention provides techniques for direct soft material to hard material fixation. As shown and explained throughout the present disclosure, frequent use is made of a tendon that is to be attached to a bone as an example. However, such a tendon-bone example is used throughout this disclosure for sake of simplicity only, and the present invention is not limited to only tendon to bone fixation. The scope of the present invention is applicable to any soft material to hard material fixation. The soft material may be biological (e.g., tendon) as well as artificial materials (e.g., grafts). The hard material may also be biological (e.g., bone) as well as artificial materials (e.g., hard plastic or metal). Examples of such biological and artificial, as well as soft and hard, materials are apparent to one having ordinary skill in the art. Thus, the use of "tendon" through this disclosure should be read as "any soft material" and the use of "bone" throughout this disclosure should be read as "any hard material."

In examples described through this disclosure, the present invention is shown as a tendon to bone fixation using a device that is easy to manufacture and use. In particular embodiments, the present invention is a modified anchor. The elegant simplicity of this invention eases the complexity of tenodesis procedures and its basic but effective design and use will make it readily adopted by the orthopedic community.

As used herein and through this disclosure, the terms "invention" and "anchor" are often used interchangeably for sake of simplicity. However, the use of the term "anchor" should not limit the embodiments of the present invention to only those devices that resemble or act as traditional anchors. The full scope of the present invention covers all concepts and designs that function in the same manner as the exemplary embodiments described herein and throughout this disclosure to assist in the fixation of tendon to bone.

The present invention, as shown in the numerous but not limiting exemplary embodiments, has applications to both open and arthroscopic procedures. The anchor has different versions, which allows it to be used for a wide array of fixation techniques. It is also available in different sizes, which allows the device to be used for the fixation of tendons of different diameters and for different applications. The anchor deployment instruments allow placement and attachment of the anchor with a single hand. The dimensions of the device are tailored for orthopedic access with standard arthroscopic equipment and can be used equally well with open procedures as well.

Exemplary anchor embodiments of the present invention provide for a substantially non-cylindrical shape having a substantially non-circular cross-section to enable compression of the graft directly against bone and securing the anchor within the bone tunnel. The substantially non-cylindrical geometry applies differential forces to compress the graft against bone tissue versus affixing the anchor within the bone tunnel. As such, the substantially non-cylindrical anchor embodiments are able to urge the graft directly against bone tissue without damaging, abrading, or tearing the graft while maintaining sufficient pull-out forces by engaging the bone tissue directly to prevent dislodgement of the anchor relative to the bone. This separation of applied forces results from the non-cylindrical geometry of the substantially non-cylindrical anchor embodiments.

Exemplary device embodiments of the present invention offer distinct advantages over current techniques. Compared to other conventional devices, such as, for example, ones described above, the present devices offer, for example, ease of insertion (no preparation of tendon end required, single handed trigger deployment), minimization of graft trauma (no rotation of tendon upon insertion, no cutting of graft with screw threads, no cutting sutures), a substantially non-cylindrical cross-section to improve fixation and graft compression, and facilitation of graft tensioning.

Compared to standard interference screw fixation, the embodiments of the invention allow direct fixation of the tendon, or other graft within the bone tunnel without a pull-through stitch needed to seat the tendon into the bone tunnel and hold tension during fixation. By further comparison to traditional techniques, the present device eliminate the need for bone tunnel preparation and the subsequent need to thread sutures and tendon through these bone tunnels. By providing aperture fixation, the embodiments of the invention minimize graft motion in the tunnels, thereby eliminating the "bungee effect" and "windshield wiper effect". Finally, they provide direct tendon to bone compression, which facilitates healing, and provides a single point of fixation, which allows for more isometric graft positioning.

Many advantages of the present invention, as shown in its various embodiments, are apparent to one having ordinary skill in the art. General categories of non-limiting examples of the advantages of the present invention include, but are not limited to: ease of preparation, ease of insertion and lack of tendon compromise. There is ease of preparation because there are no bone tunnels, minimal exposure required, and no tendon preparation (whip-stitch) needed. There is ease of insertion because there are no passing sutures through tunnels, no threading tendon through tunnels, and single handed insertion and deployment. Finally, there is no tendon compromise because there is no cutting of the graft with screw threads, and no cutting of the sutures with screw threads. These and other advantages of the present invention are described herein and apparent to those having ordinary skill in the art.

BRIEF DESCRIPTION OF THE DRAWINGS

FIGS. 4A to 4F show isometric views, side sectional view, side view, rear view, and front view of an exemplary deployment system embodiment according to the present invention with an exemplary direct tendon anchor embodiment.

FIGS. 12A to 12D show isometric view, side view, end view, and side-sectional view of the exemplary deployment instrument embodiment in FIGS. 11A to 11C securing the substantially non-cylindrical direct tendon anchor embodiment in FIGS. 8A to 8D to the tibia.

FIGS. 14A to 14D show isometric views and side views of an alternative deployment instrument embodiment according to the present invention.

FIGS. 17A to 17C show an isometric view, side-sectional view, and top view of the substantially non-cylindrical direct tendon anchor embodiment in FIGS. 8A to 8D securing a section of tendon to bone.

FIGS. 18A to 18D show side view, isometric view, side-sectional view, and top view of the substantially non-cylindrical direct tendon anchor embodiment in FIGS. 8A to 8D securing the end of a tendon to bone.

FIGS. 20A to 20D show isometric views and top view of two exemplary direct tendon anchor embodiments of the invention in an unexpanded orientation.

FIGS. 20E & 20F show isometric view and top view of the direct tendon anchor embodiments in FIGS. 20A to 20D in an expanded orientation.

FIGS. 21A to 21D show side-sectional view, and cross-sectional views of the direct tendon anchor embodiment in FIGS. 20A to 20F securing the strands of a tendon to bone.

FIGS. 24A to 24D show side views, side-sectional view, and top view of the substantially non-cylindrical direct tendon anchor embodiment in FIGS. 23A to 23D securing the end of a tendon to bone.

FIGS. 25A to 25F show top views, isometric view, cross-sectional view, side view, and side-sectional view of the substantially non-cylindrical direct tendon anchor in FIGS. 23A to 23D securing a segment of tendon to bone.

FIGS. 30A to 30C show isometric view, top view, and side view of an alternative substantially non-cylindrical direct tendon anchor embodiment according to the present invention.

FIGS. 30D to 30F show isometric view, top view, and side shaded view of the substantially non-cylindrical direct tendon anchor embodiment in FIGS. 30A and 30B in an expanded orientation.

FIGS. 32A to 32C show isometric view, side view, and top view of an alternative direct tendon anchor embodiment according to the present invention.

FIGS. 42A to 42D show isometric views, side view, and top view of a substantially non-cylindrical multiple component tendon anchor embodiment according to the present invention.

FIGS. 46A to 46D show isometric views, side view, and top view of a substantially non-cylindrical multiple component tendon anchor embodiment according to the present invention.

DETAILED DESCRIPTION OF THE INVENTION

Figure 1A:
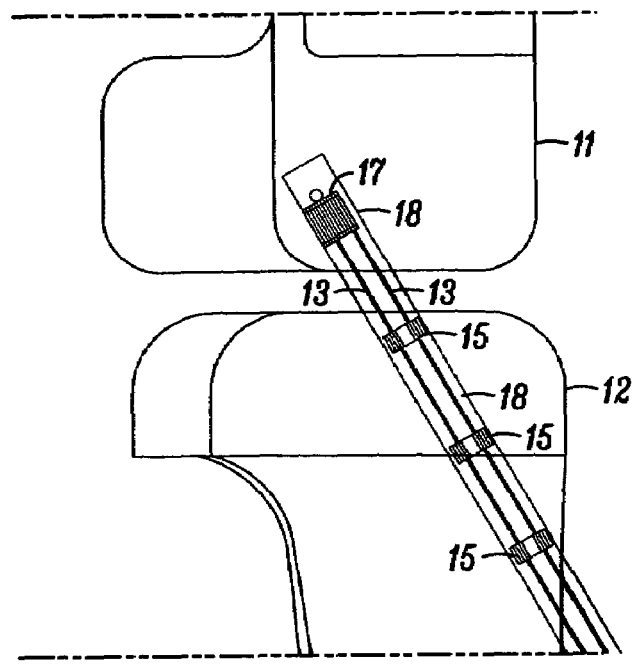
FIGS. 1A and 1B show a side view and side-sectional view of a femur and tibia with an ACL graft secured to the bones using exemplary tendon anchor embodiments according to the present invention.

The present invention relates to devices, systems and methods that enable the direct fixation of tendons, and/or soft tissues to bone for the repair of torn or diseased tendons, or the reconstruction of unstable joints. The various embodiments are applicable to surgical procedures that require direct fixation of tendon to bone. This includes a wide array of procedures including, but not limited to, the shoulder, elbow, wrist, hand, knee, ankle, and foot.

In describing the present invention and its various components, a general overall description is presented for each of the components that may be used in the fixation system, including an implantable anchor and associated equipment. This general description is not to be taken in a limiting sense, but is made merely for the purpose of illustrating certain general principles of the various embodiments of the present invention, and may be noted in one or more of such exemplary embodiments presented in FIGS. 1-48. Certain exemplary embodiments of the present invention, and many features and advantages of those exemplary embodiments, will be elaborated in more detail in the following detailed description and accompanying drawings.

Implantable Anchor

The exemplary device embodiments of the invention provide a variety of bone anchors that allow fixation of tendon or other soft tissues directly to bone without requiring suture fixation of the tendon to the bone. Conventional bone anchors have typically been tacks, which allow the pinning of adjacent tissues to bone; or suture anchors, which attach a suture to bone and the suture to the soft tissue to indirectly attach soft tissue to bone. The implant embodiments of the present invention provide direct attachment approaches that use the anchor itself (rather than attached sutures) to directly hold and stabilize the tendon or other soft tissue into bone tunnels or holes.

Direct anchor embodiments include uniquely shaped implants that hold a tendon or other soft tissue, and fix it directly to bone. The direct anchor can, but does not always have to, be substantially non-cylindrical anchors having a non-circular cross-section, for example, bi-lobed (e.g., "butterfly" shaped), "clover-leaf" shaped, rectangular, and/or shaped with grooves or openings configured to differentially compress the tendon, or other soft tissue, directly against bone, and affix the anchor within the bone channel. In addition, the direct anchor can incorporate expandable arms that compress the tendon or other soft tissue directly against bone while directly contacting the bone to provide anchoring of the implant. These direct anchor embodiments may be single or multi-component implants that allow for implant expansion by use of wedge elements. They can further include features such as grasping tines to prevent tendon (or other soft tissue) slippage during deployment and after attachment, and attachment tabs to prevent migration of the anchor from the bone hole or tunnel once positioned and secured in place.

Some classes of anchors are substantially symmetrical but have the characteristic of expanding wall portions or pivoting arms that aid in the press fit of the anchor within a hole in a bone. These anchors also typically have tabs or other gripping portions that serve to lock the anchor in place within the bone hole.

In addition, the direct anchor embodiments can incorporate "docking slots" which allow sutures to augment or replace the direct attachment of the tendon, or other soft tissue, to bone. These direct anchor embodiments can also incorporate groves to secure and align the tendon along the implant prior and during implant deployment. This alignment feature minimizes or prevents the tendon from interfering with the anchor to bone contact needed for optimal anchoring of the implant.

Associated Equipment

The insertion of the direct anchor may be standardized with the use of a corresponding equipment tray. The initial procedural step may involve the use of a guide pin which allows the accurate localization and directionality of the bone hole, through which the tendon, or other soft tissue, is inserted and secured with the direct anchor. A cannulated drill of appropriate size can be used to create a drill hole over the guide pin. The drill has a depth stop to allow accurate depth for the anchor. The tray can hold a variety of drill sizes ranging from 3 mm to 12 mm in diameter. Finally the tray may have a device used to determine the diameter of the tendon that will be directly secured to the bone within the drilled hole.

Surgical Techniques

To accomplish tendon fixation using the exemplary methods and devices described herein, standard surgical preparation of the site and/or arthroscopic portals for access of the region are performed. The joint is dilated with arthroscopic fluid if the procedure is to be performed arthroscopically. With open procedures, the device may easily be manipulated and deployed with a single hand. For arthroscopic procedures, the deployment device is introduced through a standard 5, 6 or 8 mm cannula placed into the joint. A range of cannula sizes would be 2-11 mm.

The direct anchor devices as described in the present invention may be used with a variety of techniques. The specific details of the technique will vary depending on the anatomic structure being repaired and the device embodiments of the invention. An example of four specific uses will be described to demonstrate the versatility of the present implant embodiments according to the present invention. The techniques relate to classes of procedures rather than individual procedures. They are generally described here and will be presented in more detail below:

A. Suturing the tendon to the implant prior to insertion. This technique is used in cases when the length of available tendon is limited. The technique requires an open surgical dissection to prepare the end of the tendon, and to suture it to the anchor;

B. Double tendon strand technique. This technique is used when the available tendon is abundant, or when a tendon requires fixation at its mid-point;

C. Sliding anchor technique. This technique allows for the fixation of tendons that are protruding out of a bone tunnel. Rather than pushing the tendon-anchor construct into the tunnel simultaneously, the anchor is slid along (or with) the tendon, into position, prior to deployment.

D. Rotator cuff repair technique. This technique uses the shape of the implant to act as a pulley to draw the rotator cuff margin into a bone tunnel.

Each of the above general classes of procedure will be described in more detail, including the general steps required to perform each procedure. It should be understood that these four types of procedures are not the entire scope of the present invention. Other procedures may also utilize the present invention as long as a goal is to secure tendon, or other soft tissue, to bone, or other hard or stable tissue. Such other procedures, whether currently in existence or to be developed in the future, may use the present invention, and thus such procedures using the present invention are within the scope of the present invention.

A. Suture Reinforced Technique

The tenodesis of some tendons is limited by the length of the tendon. Repair of the distal biceps of the elbow is an example of this type of procedure. In this situation, the tendon may not be long enough to achieve two-point compression between the deployed anchor and the tendon. Two-point compression is achieved by other techniques using the embodiments of the present invention, as described below, by looping the tendon around the anchor such that two segments of tendon are engaged by the direct anchor and compressed directly against bone tissue.

Since tendon to bone compression in the suturing technique will occur on only one tendon surface, the repair can be reinforced by suturing the tendon to the anchor prior to or after insertion. This serves to minimize tendon slippage during insertion, and provides a second point of fixation after anchor deployment.

The procedure starts with preparation of the tenodesis site, which is initially prepared by dissecting the soft tissues from the region. This can be done with an open technique or arthroscopically depending on the procedure performed. A guide pin is then placed into the bone to the depth and direction desired for the bone tunnel. A cannulated drill is drilled over the top of the guide pin to create the tenodesis hole.

The next step involves exposing the tendon end that is in need of repair. A non-absorbable grasping stitch is placed at the end of the tendon, which can be used for traction and repair. The tendon is traditionally prepared with an open or limited open exposure, but can be prepared arthroscopically in some instances. The grasping suture is then applied to the lateral margins of the anchor, seating them firmly into the "docking" slots. With the tendon pulled tight against the anchor, the tendon is wrapped around the tip of the anchor where grasping tines help prevent slippage. The suture is then tied over the top of the tendon body, creating two points of fixation onto the anchor.

Once the tendon is fixed to the anchor, the tendon may be inserted into the pre-drilled bone hole. The tendon-anchor assembly will fit snugly into the hole and should be inserted to the level of the stop placed on the anchor deployment device. Once seated, the anchor is deployed by squeezing the hand-held trigger mechanism. Anchor deployment results in compression of the anchor against the surrounding bone, and also compresses the tendon against the bone. Once deployed, the deployment instrument is simultaneously released from the anchor, leaving only the tendon-anchor construct firmly attached to bone. A trailing suture can be attached to the anchor and be used to reinforce the repair if needed.

2. Double Tendon Strand Technique

Many tenodesis procedures require the fixation of two tendon strands simultaneously. In addition, some tenodesis procedures can be performed more easily by fixing two tendons simultaneously and then amputating the arm of the tendon not needed. This variation allows for two-point tendon to bone compression and increases surface area of contact between the tendon and bone tissue, which accelerates healing.

Two tendon arms can be fixed simultaneously by using an implant that straddles and supports the tendon into its bone tunnel. This technique can be used in most scenarios that would traditionally use a bone bridge to fix the tendon into position. Common examples of this type of fixation include the distal fixation for elbow collateral ligament reconstructions, proximal fixation of hamstring reconstructions, and the fixation of the long head of the biceps tendon in the shoulder.

Since tendon to bone compression occurs on two surfaces simultaneously, direct tendon compression to bone is sufficient to prevent tendon slippage during insertion. As a result, the tendon does not need to be sutured to the anchor prior to or after insertion.

The procedure starts with preparation of the tenodesis site, which is initially prepared by dissecting the soft tissues from the region. This can be done with an open technique or arthroscopically, depending on the procedure performed. A guide pin is placed into the bone to the depth and direction desired for the bone tunnel. A cannulated drill is drilled over the top of the guide pin to create the tenodesis hole.

With double strand tenodesis, the end of the tendon does not need to be prepared, though some type of traction suture may be placed to facilitate tensioning and positioning of the tendon. With the tendon positioned and tensioned over the bone hole, the anchor is placed over the top of the tendon. The arms at the tip of the anchor then straddle the tendon, supporting it as it is pushed into the bone tunnel. The tendonanchor-tendon assembly fits snugly into the hole and should be inserted to the level of the stop placed on the anchor deployment device. Once seated, the anchor is deployed by actuating a hand-held trigger mechanism. Anchor deployment results in compression of the anchor against the surrounding bone, and direct compression of the two tendon strands against bone. Once deployed, the deployment instrument is simultaneously released from the anchor, leaving only the tendon-anchor-tendon construct firmly attached to bone. A trailing suture attached to the anchor can be used to reinforce the repair if needed.

3. Sliding Anchor Technique

Some surgical procedures require the fixation of tendon strands within and/or as they extend from a bone tunnel. Here the tendons have been placed from the opposite side and need fixation from a different direction. Other times a tendon may already be inserted into a hole and may merely need fixation in its current position. A modified anchor (sliding anchor) may be used to provide this fixation. Examples where this type of fixation is needed are the tibial fixation of hamstring anterior cruciate ligament reconstructions and the humeral fixation of elbow collateral ligament reconstructions.

The sliding anchor is similar to the standard tenodesis anchor except that it does not expose grasping tines, which prevent the anchor from sliding, during insertion. These anchor embodiments need to slide between the tendon, or graft, strands into a position that is desired before deployment.

With this technique, the bone tunnel has already been created and the tendon strand(s) are already either seated into the tunnel, or are protruding from the tunnel. Traction is pulled on the tendon arms, either with direct pull or via traction sutures placed at the tendon end. The free anchor is then positioned to slide between the tendon arms into its desired position. At times, this is at the most external position in the tunnel, and at other times advanced deep into the tunnel. Once the anchor is in the appropriate position, with traction placed on the tendon ends, the anchor is deployed manually by actuating the single-hand trigger mechanism of a deployment instrument. As the anchor is deployed it is expelled from the deployment instrument, leaving the deployed direct anchor implant behind. The result is an anchor providing direct lateral compression of the tendon strands into the bony tunnel. A trailing suture attached to the anchor can be used to reinforce the repair if needed.

4. Rotator Cuff Repair Technique

The repair of rotator cuff tears can be performed utilizing the unique shape of this implant. Repairing a rotator cuff tear into a trough is a technique often used during open procedures but difficult to perform arthroscopically. The shape of this anchor facilitates rotator cuff repair into a trough utilizing a sliding suture technique.

Whether performed arthroscopically or through an open incision, the greater tuberosity is debrided with a mechanical shaver down to bone. A round burr is then used to create a bone trough in the tuberosity in an area that allows the cuff tissue to be repaired with minimal tension. A drill hole is placed in the depth of the trough at its lateral margin. A mattress suture is then passed into the lateral margin of the rotator cuff with the suture strands exiting superiorly.

These sutures are then pulled out the lateral portal and threaded through tunnels in the anchor. With traction placed on the rotator cuff stitch, the anchor is inserted into the joint and positioned adjacent to the rotator cuff margin. With various amounts of traction, the anchor is pushed into the drill hole, pulling the cuff margin into the trough. With the correct amount of traction, the rotator cuff margin is pulled into the trough just above the anchor. The anchor is then deployed and the sutures wedged into the anchor, creating a knotless rotator cuff repair.

The process can be repeated as needed to get the margin to firmly seat into the bone trough. This technique utilizes the anchor to grasp the suture and fix it to bone, eliminating the need for arthroscopic knot tying. The primary strength of the repair is related to the anchor grasping the suture. The most difficult step in fixation is then made knotless.

Other Potential Uses of the Tenodesis Anchor

It should be appreciated that the tenodesis anchor can be used for other indications involving the fixation of soft tissue to bone. The embodiments of this invention as presented herein and in the figures are tailored to human anatomy. Additionally, the present invention may also be tailored for use in other species such as horses, dogs, sheep, and pigs as well as invertebrates. One having ordinary skill in the art could reconform the exemplary embodiments described herein without undue experimentation to fit or be suitable for animals other than humans. Such new configurations for use in non-human subjects are also within the scope and spirit of the present invention.

The size and scope of the invention described provides additional advantages that include, but are not limited to: providing an arthroscopic approach for the tenodesis of tendons; reduction in the visible scars associated with open surgical procedures by using small port access allowed by the deployment device; reducing the complexity associated with arthroscopic knot tying; and reducing the required surgical time as well as the level of complexity associated with these procedures.

The use of devices according to the present invention may be applied to virtually all orthopedic procedures requiring fixation of tendon, or other soft tissue, to bone. The invention is useful for procedures whether performed with open dissection or with arthroscopic techniques. Non-limiting examples include, but are not limited to: (a) shoulder (rotator cuff repair, long head of biceps tenodesis); (b) elbow (distal biceps tendon repairs, medial (ulnar) collateral ligament reconstruction—the "Tommy John Procedure", lateral ulnar collateral ligament reconstruction—for posterolateral rotatory instability of the elbow); (c) wrist (carpal instability—scapholunate and lunotriquetral ligament reconstructions, Blatt Capsulodesis, thumb carpometacarpal arthroplasty (ligament reconstruction with tendon interposition—LRTI)); (d) hand (chronic thumb ulnar collateral ligament reconstruction (Gamekeeper's thumb), chronic thumb radial collateral ligament reconstruction, finger metacarpophalangeal ligament reconstruction); (e) knee (hamstring anterior cruciate ligament reconstruction—proximal and distal fixation, medial collateral ligament repair/reconstructions with autograft or allograft, lateral collateral ligament repair/reconstruction with autograft or allograft, posterolateral reconstruction with autograft or allograft); (f) ankle and foot (various lateral collateral ligament reconstructions (Watson-Jones/Chrisman Snook)), posterior tibial tendon repair or reconstruction). Other procedures are also within the scope of the present invention as long as such procedures could benefit from the use of devices, systems or methods according to the present invention.

Various embodiments, general descriptions, and procedures utilizing the exemplary embodiments of the present invention have been described above. Such general descriptions are applicable to many of the exemplary embodiments shown in FIGS. 1-48 and described in further detail below. It should be noted that the specific descriptions of the specific exemplary embodiments presented below should also be considered in view of the general descriptions, procedures and processes already described above. Such general descriptions, procedures and processes will not be repeated again with every specific embodiment presented below for sake of clarity. However, it should be noted, and as is apparent to one having ordinary skill in the art, that descriptions of the various embodiments presented below are supplemented by features and properties shown and recognized, and gleaned from the figures as well as the general descriptions already presented above.

Direct Tendon Anchoring Embodiments

Figure 1B:
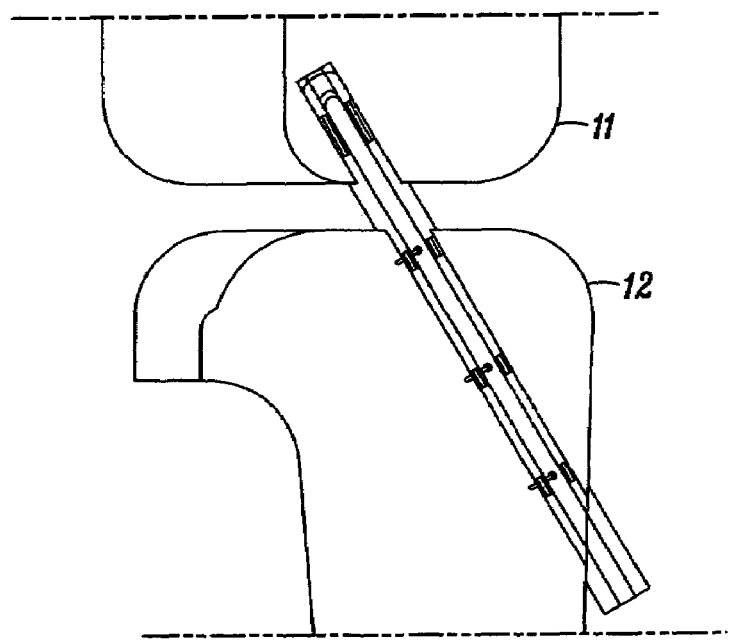
Figure 2:
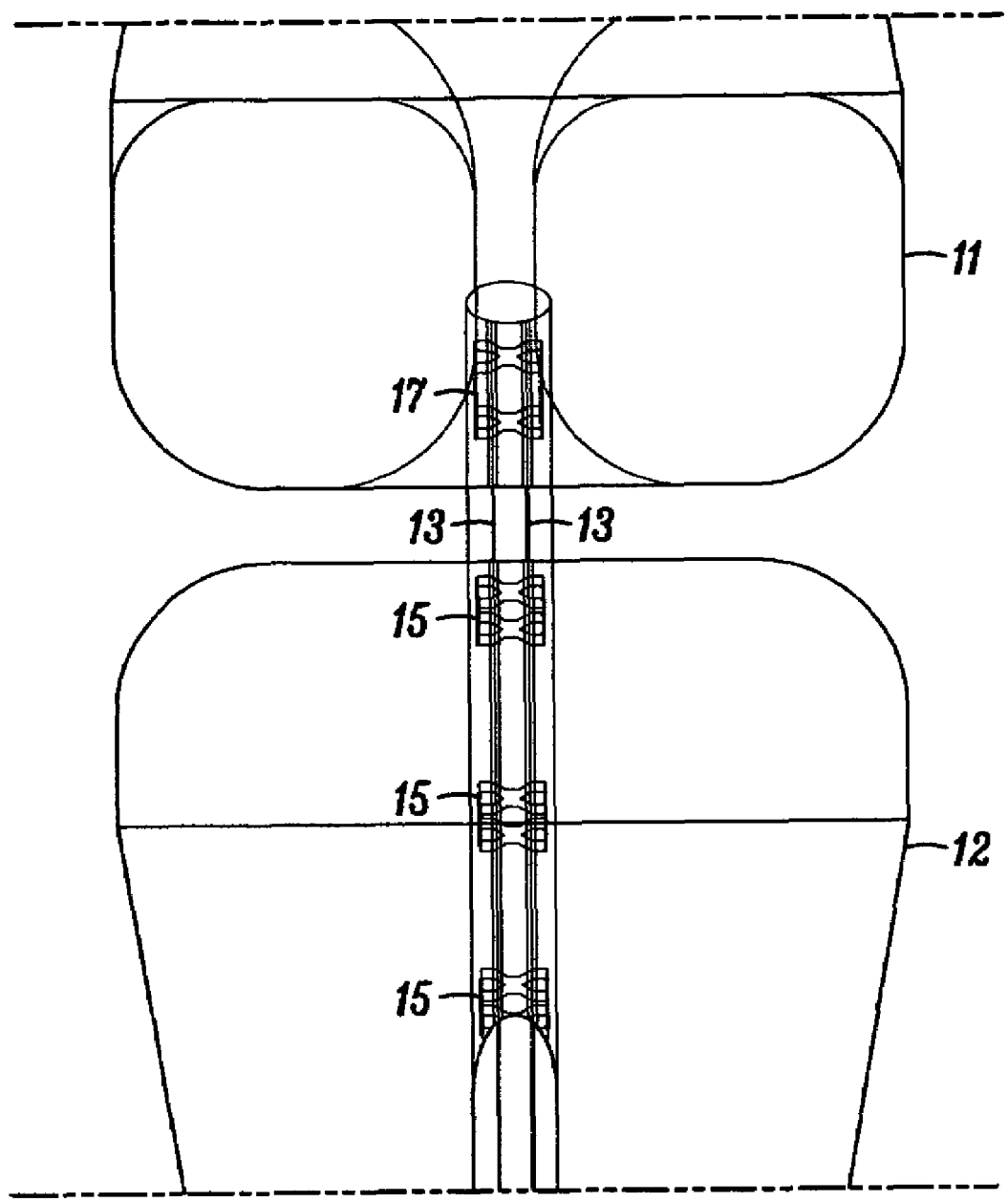
FIG. 2 shows a frontal view of a femur and tibia with an ACL graft secured to the bones using exemplary tendon anchor embodiments according to the present invention.

FIGS. 1A and 1B show a side view and a side-sectional view of a hamstring anterior cruciate ligament (ACL) reconstruction with exemplary direct tendon anchor embodiments used to secure the ACL graft proximal to the femur 11 and distal to the tibia 12. FIG. 2 shows a front view of the ACL reconstruction shown in FIGS. 1A and 1B. As shown in FIGS. 1A, 1B, and 2, one exemplary direct tendon anchor 17 is used to secure the wrapped two strand hamstring graft 13 to the femur 11 by inserting the anchor through a drilled bone hole 18 created completely through the tibia 12 and partially through the femur 11. Three direct tendon anchors 15 are shown to secure the free ends of the hamstring graft strands 13 to the tibia 12. It should be noted than any number of direct tendon anchors (1 to 5) can be utilized to secure the graft within the drilled bone hole.

FIGS. 3A to 3D show an isometric view, an end view, a shaded isometric view, and an isometric view, respectively, from the opposing end for one exemplary direct tendon anchor device 31 embodiment of the invention. This direct anchor embodiment 31 can be utilized to separately secure all discrete four strand ends of the hamstring ACL graft within a bone. Alternatively, the exemplary direct anchor embodiment 31 can be utilized to secure two strand tendons or single strand tendons, or grafts, within a drilled bone hole.

Figure 3A:
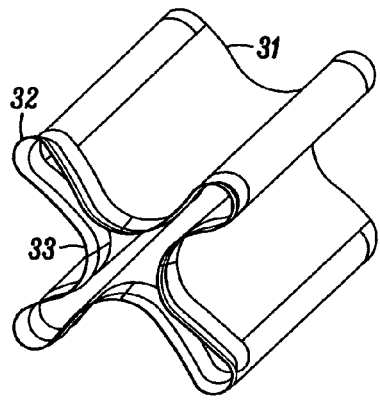
FIGS. 3A to 3D show isometric and rear views of an exemplary direct tendon anchor embodiment according to the present invention.
Figure 3B:
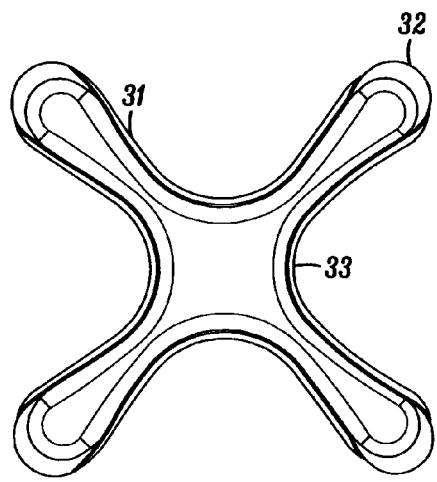
Figure 3C:
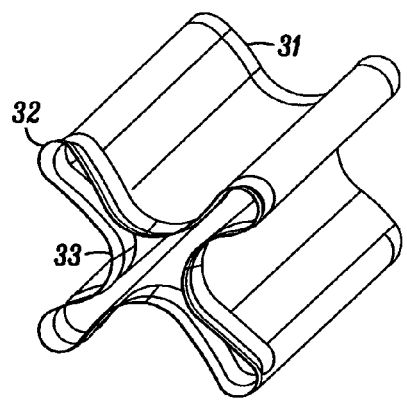

As shown in FIGS. 3A to 3C, one end 32 of the exemplary direct anchor embodiment is flared at the "clover leaf" extensions to partially penetrate into bone and increase the surface area of the contacting segment between the direct anchor embodiment and the surface of the bone defined by the drilled hole. The mid-section 33 between these "clover leaf" extensions are not flared to ensure the direct anchor is able to expand into a radially enlarged orientation during deployment, ensuring the direct anchor compresses the tendon against the bone surface defined by the drilled hole.

Figure 3D:
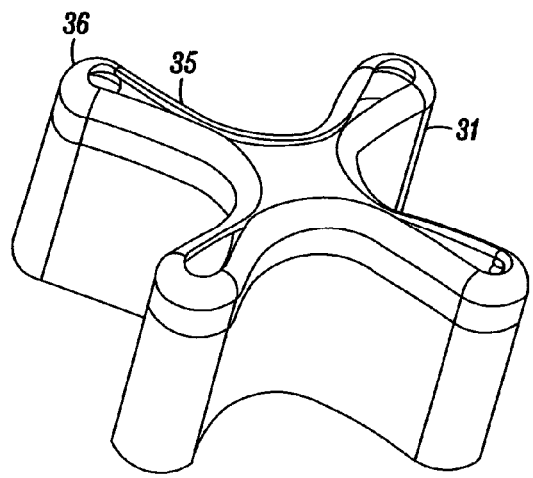

As shown in FIG. 3D, the opposite end of the direct anchor embodiment 31 can incorporate an inward radius 36 to increase the surface area of contact between the tendon and direct anchor 31, and provide an atraumatic surface between the direct anchor 31 and tendon strands that loop around this end 35 of the direct anchor 31. This anchor embodiment 31 can be used to secure the proximal, looping end of the hamstring ACL graft within the femoral drilled bone hole or other sliding anchor applications where a tendon or graft is looped around the anchor. In addition, this anchor embodiment 31 can be used to secure tendon or grafts within drilled bone holes using the double tendon strand technique, as described above. During the double tendon strand technique, the tendon strand loops around this end of the direct tendon anchor wherein the radiused end 35 prevents damage to the tendon or graft caused by contact with the direct anchor 31.

FIG. 4A shows an isometric view of an exemplary deployment instrument 41 according to the present invention. FIGS. 4B to 4F show an isometric view, a side-sectional view, a side view, a rear end view, and a front view, respectively, of the exemplary deployment instrument in FIG. 4A with a direct anchor 42 supported for deployment. This exemplary deployment instrument 41 includes a movable anvil 43 that incorporates a transition from the pull rod 44 to the distal expanding dilator 45. The distal end of the dilator contains a radius 46 to prevent trauma to the tendon as the instrument 41 positions the direct anchor 42 and secures the tendon within the drilled bone hole while expanding the direct anchor 42. The deployment instrument 41 incorporates a holding shaft 47 to support the direct anchor 42 while the dilator 45 is actuated thereby expanding the direct anchor 42 into an enlarged orientation. The holding shaft 47 incorporates protrusions 48 that fit inside the "clover leaf" extensions of the direct anchor 42.

Figure 5A:
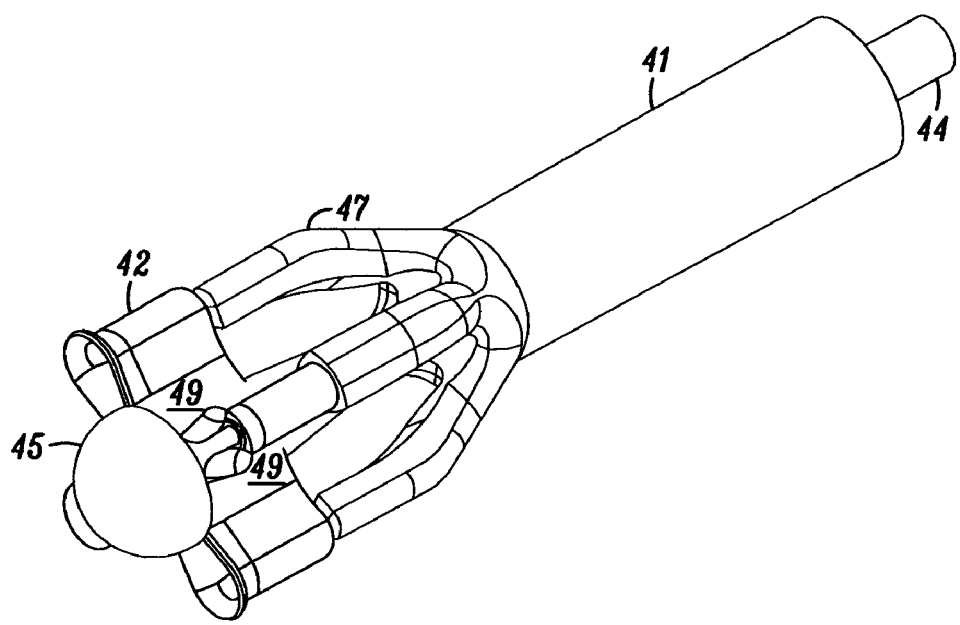
FIGS. 5A and 5B show isometric views of the exemplary deployment system embodiment in FIGS. 4A to 4F with a dilator mechanism retracted to expand the direct tendon anchor.
Figure 5B:
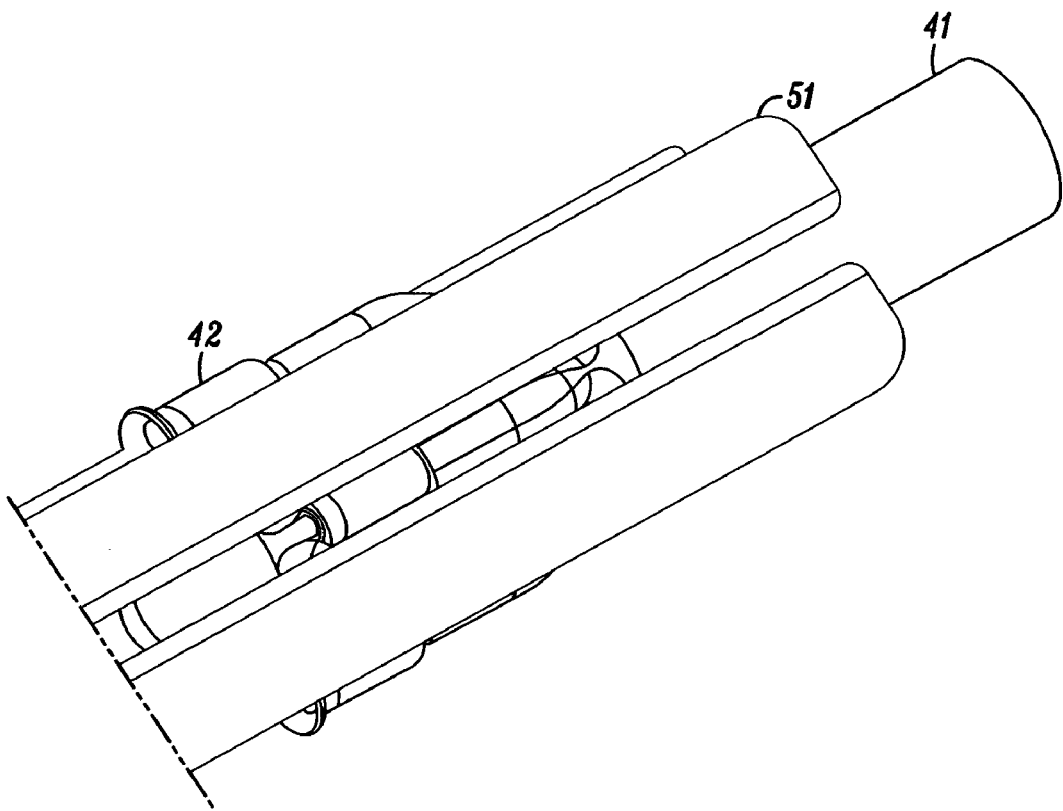

FIGS. 5A and 5B show the exemplary deployment instrument 41 in FIGS. 4A to 4F with the dilator 45 retracted. FIG. 5B shows a four strand tendon graft 51 (commonly used during the hamstring ACL reconstruction) positioned with each strand 51 held within a groove 49 of the direct anchor 41. It should be noted that two strands or a single strand looped or with one end free can be supported within the grooves 49 of the direct anchor 41. As the dilator 45 is retracted, the innermost grooves 49 of the direct anchor 41 are deformed outwardly thereby compressing the tendons 51 supported within the grooves 49 against the surface defined by the drilled bone hole. In addition, the "clover leaf" extensions are further expanded outward into engagement with the bone thereby securing the direct anchor 41 thus the supported tendon within the drilled bone hole.

Figure 6:
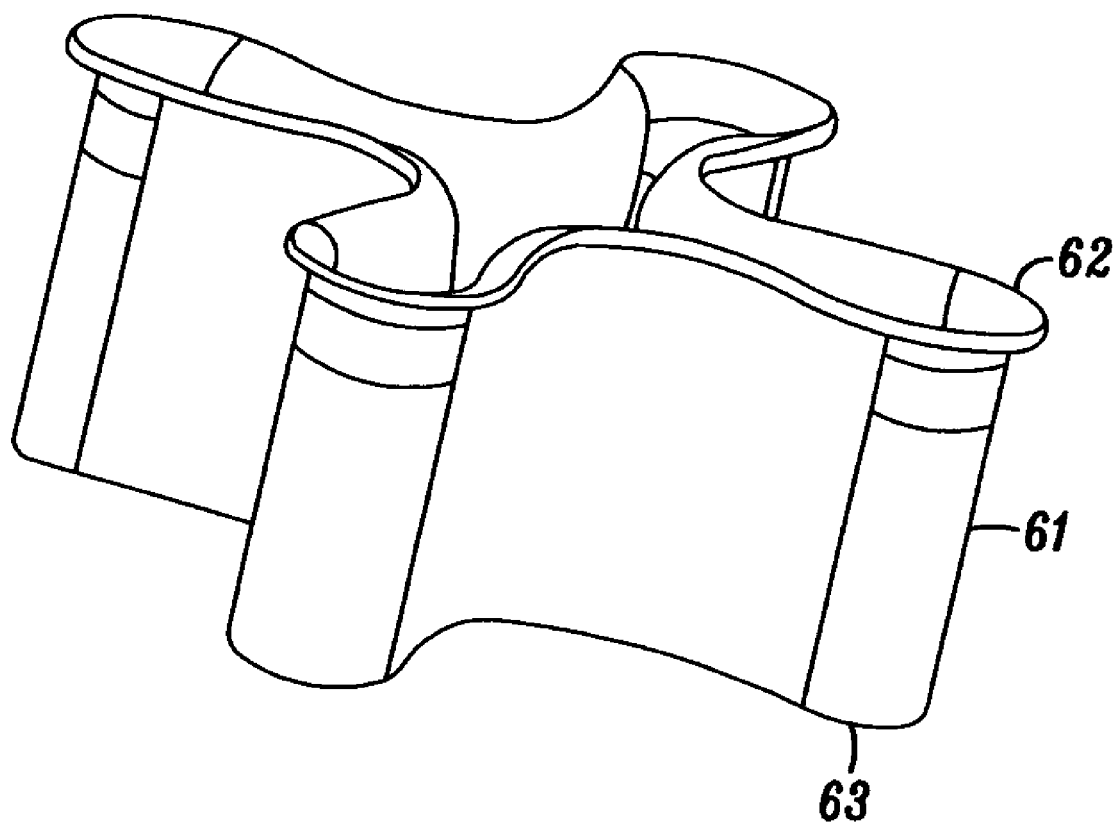
FIG. 6 shows an isometric view of an exemplary direct tendon anchor embodiment according to the present invention.

FIG. 6 shows an alternative direct anchor embodiment 61 where one end 62 of the direct anchor is flared throughout one edge. In this embodiment, the opposite end 63 of the direct anchor 61 is straight. It should be noted that the flared end 62 can be flared along the entire periphery of the direct anchor 61, as shown; or it could be flared only at the "clover leaf" extensions as shown in FIGS. 3A to 3C with the mid region defined by the grooves straight to facilitate expansion of the direct anchor. As the direct anchor embodiment 61 is expanded into an enlarged orientation, the tendon is compressed against the bone-drilled surface and the "clover leaf" extensions are pressed into the surface of the bone defined by the drilled bone hole. The flared end 62 increases the bond strength between the direct anchor 61 and the bone surface by increasing the surface area of contact between the bone and the anchor 61 and ensuring any tension applied to the bone anchor 61 is distributed over a large surface that deflects the applied forces in a non-axial direction to increase contact upon further deflection of the bone anchor.

Figure 7:
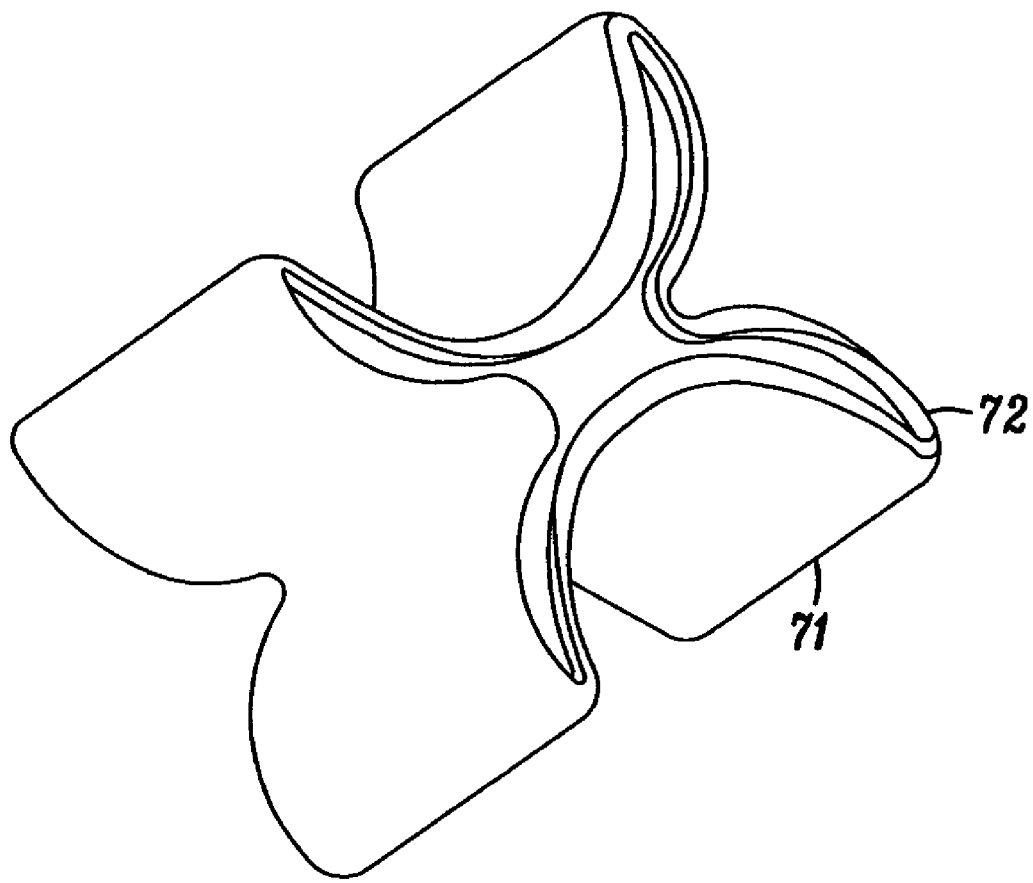
FIG. 7 shows an isometric view of a substantially non-cylindrical direct tendon anchor according to the present invention.

FIG. 7 shows an isometric view of a substantially non-cylindrical direct anchor embodiment 71 designed to secure a single strand looped around the direct anchor 71, two strands looped around the direct anchor 71, or one or two tendon free ends to the surface defined by the drilled bone hole. This direct anchor embodiment 71 incorporates an inward radius along one end 72 to prevent trauma to looping tendon, or graft, segments. The non-circular cross-section of this anchor embodiment 71 enables the change of applied forces that compress the graft (e.g., tendon) against bone tissue versus the forces that the anchor 71 applies against the bone tissue required to ensure the pull-out forces are high enough that the anchor 71, thus the compressed graft, will not dislodge from the bone channel. These variable forces prevent abrading, tearing, or otherwise damaging the graft while deploying the anchor 71 or supporting the graft once the anchor 71 is affixed within the bone channel.

Figure 8A:
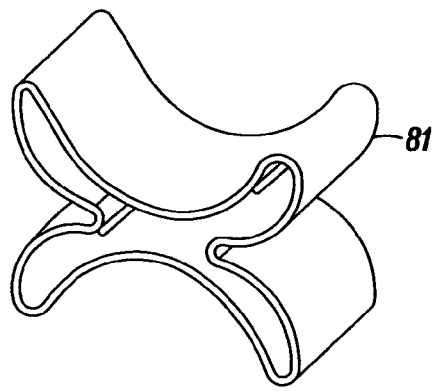
FIGS. 8A and 8B show isometric and top view of a substantially non-cylindrical direct tendon anchor embodiment in an unexpanded orientation according to the present invention.
Figure 8B:
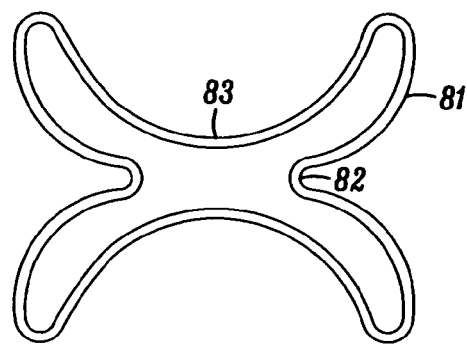
Figure 8C:
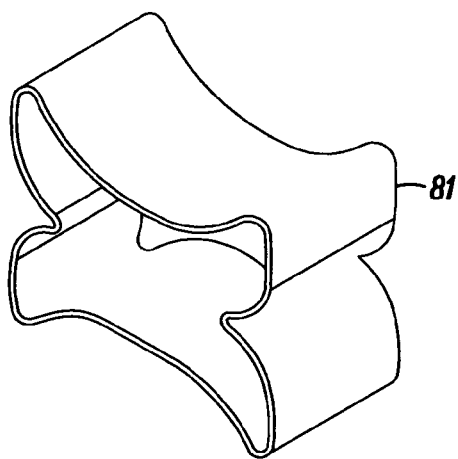
FIGS. 8C and 8D show isometric and top view of the substantially non-cylindrical direct tendon anchor embodiment in FIGS. 8A and 8B in an expanded orientation.
Figure 8D:
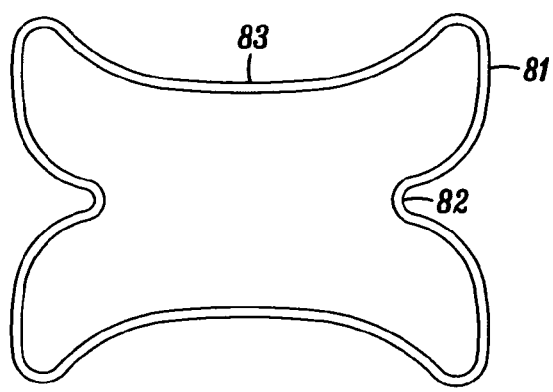

FIGS. 8A and 8B show an isometric view and a top view of another substantially non-cylindrical direct anchor embodiment 81 of the present invention. FIGS. 8C and 8D show an isometric view and a top view of the direct anchor embodiment 81 shown in FIGS. 8A and 8B in an expanded orientation. As the dilator 45 of the deployment instrument 41 is actuated, as shown in FIGS. 4A to 4F, and 5A and 5B, the inner grooves 82 and 83 of the direct anchor 81 are expanded radially thereby causing the "butterfly" extensions to deform radially outward into engagement with the bone surface defined by the drilled hole.

Figures 9A, 9B:
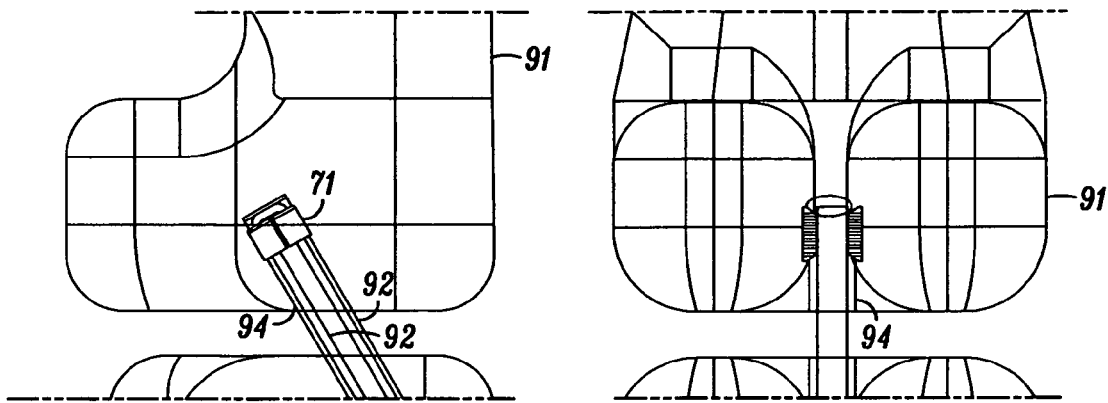
FIGS. 9A and 9B show side view and front view of the substantially non-cylindrical direct tendon anchor embodiment in FIGS. 8A to 8D securing an ACL graft to the femur.
Figures 9C, 9D:
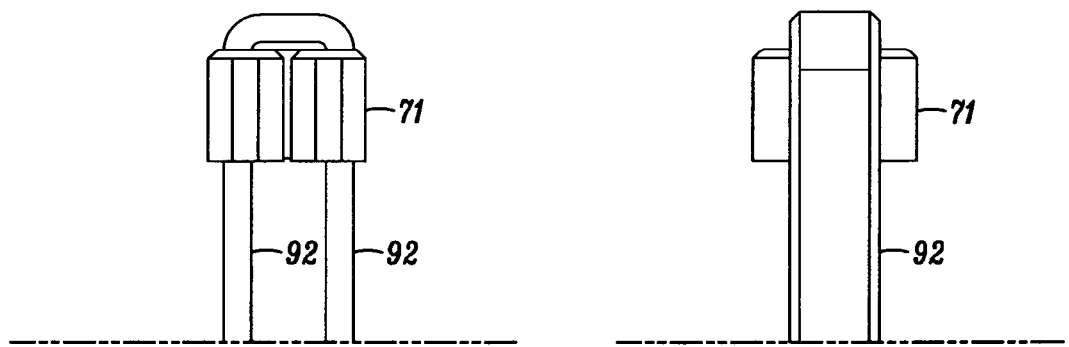
FIGS. 9C and 9D show a side view and front view of the substantially non-cylindrical direct tendon anchor embodiment in FIGS. 8A to 8D with an ACL graft positioned around the anchor.

FIGS. 9A and 9B show a side and front view of a femur 91 with two strands 92 of a hamstring ACL graft looped around the exemplary substantially non-cylindrical direct anchor 71 of FIG. 7. As shown in FIGS. 9C and 9D, the substantially non-cylindrical direct anchor embodiment of FIG. 7 can be used to connect any looping (or free end) tendon or graft to the bone surface defined by the drilled hole 94.

Figure 10A:
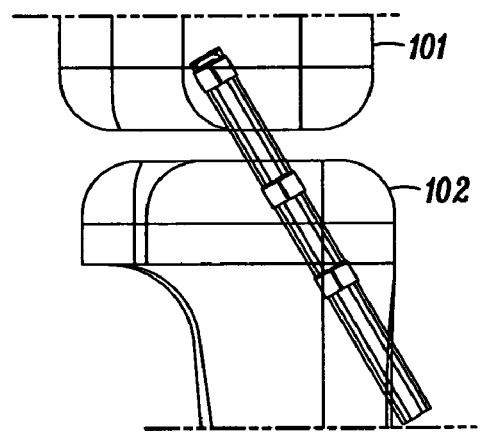
FIGS. 10A to 10D show a side view, front view, and end views of the substantially non-cylindrical direct tendon anchor embodiments of FIGS. 8A to 8D securing an ACL graft to the femur and tibia.
Figure 10B:
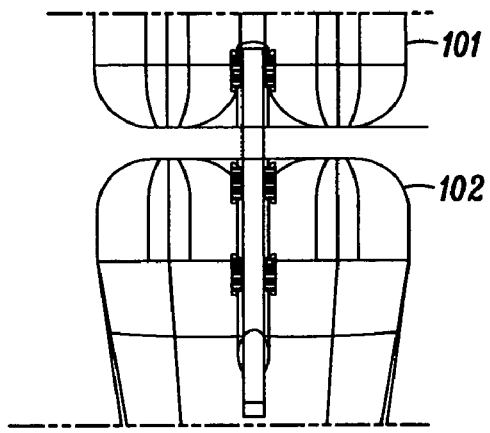
Figure 10C:
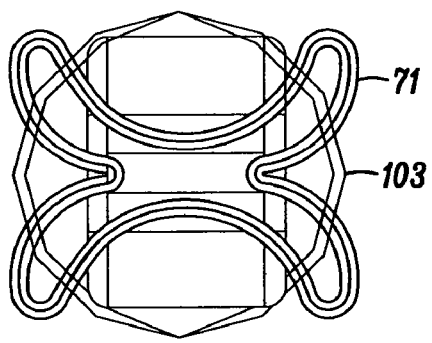
Figure 10D:
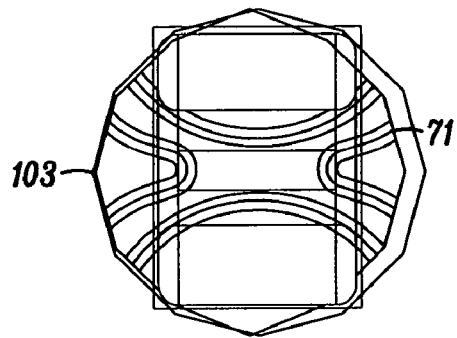

FIGS. 10A to 10D show a side view, a front view, an end view, and a cross-sectional view of the substantially non-cylindrical direct anchors in FIGS. 7 and/or 8 used to secure an ACL graft at the femoral end 101 and the tibial end 102. As shown in FIGS. 10C and 10D, the "butterfly" extensions of the direct anchor 71 are deflected into the surface 103 of the bone defined by the drilled hole to ensure engagement between the direct anchor 71 and the bone 101 or 102 as the direct anchor 71 is expanded with the deployment instrument 41.

Figure 11A:
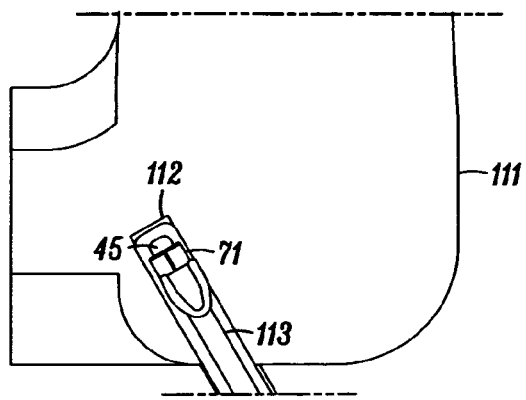
FIGS. 11A to 11C show side views of the steps for securing an ACL graft to the femur with an exemplary deployment instrument embodiment and a substantially non-cylindrical direct tendon anchor embodiment according to the present invention.
Figure 11B:
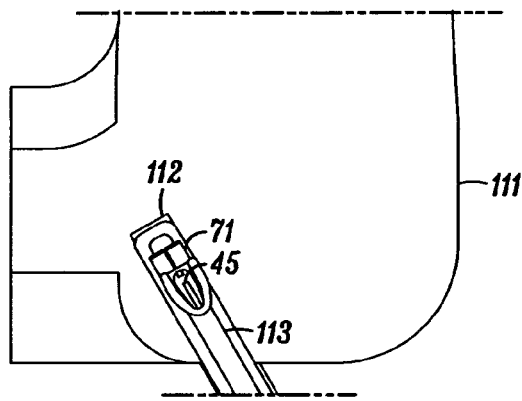
Figure 11C:
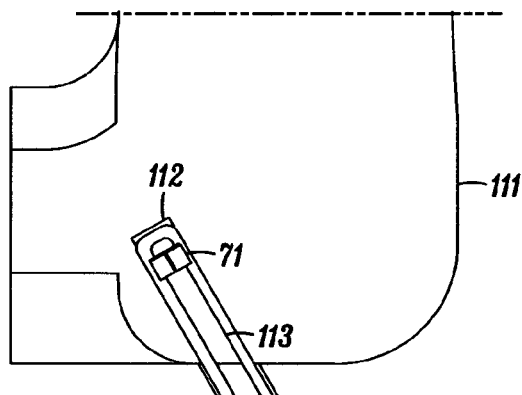

FIGS. 11A to 11C show side-sectional views of exemplary steps that may be taken in positioning and securing an ACL graft 113 within a hole 112 drilled into the femur 111 using substantially non-cylindrical direct anchor embodiments 71 or 81 shown in FIGS. 7 and 8. After drilling the bone hole 112 into the femur 111, the ACL graft strands 113 are looped around the distal end of the direct anchor 71 and inserted through the bone hole 112 of the femur 111. Once positioned, the dilator 45 is actuated to expand the direct anchor 71 into the drilled bone hole 112. Once actuated, the direct bone anchor 71 compresses the tendon 113 against the surface of the femur 111 defined by the drilled hole 112 and engages the securing extensions of the direct anchor 71 against the bone surface to ensure the tendon 113 is secured in place as tension is applied.

FIGS. 12A to 12D show an isometric view, a side view, a cross-sectional view, and a side-sectional view of the deployment instrument 41 in FIG. 4A with the substantially non-cylindrical direct anchor embodiment 71 of FIGS. 7 and 8 positioned for placement. As shown in FIGS. 12B and 12D, the deployment instrument 41 is positioned between the strands 122 of the ACL graft free ends to secure the ACL graft 122 to the tibia 121. After placement, the dilator 45 is actuated thereby expanding the direct anchor 71 inside the drilled bone hole 123, compressing the tendon free ends 122 against the bone surface defined by the drilled hole 123 and engaging the securing extensions of the direct anchor 71 against the bone 121.

Figure 13A:
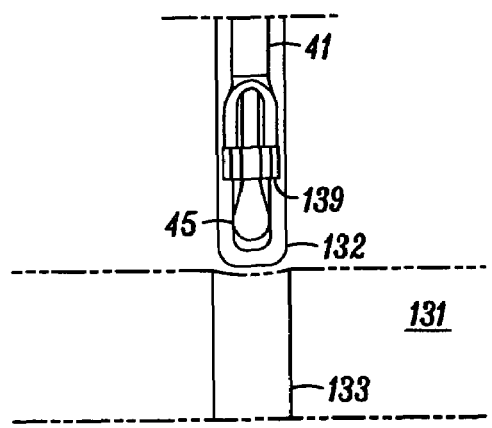
FIGS. 13A to 13D show side views of the steps for securing a tendon to bone with an exemplary deployment instrument embodiment and a substantially non-cylindrical direct tendon anchor embodiment according to the present invention.
Figure 13B:
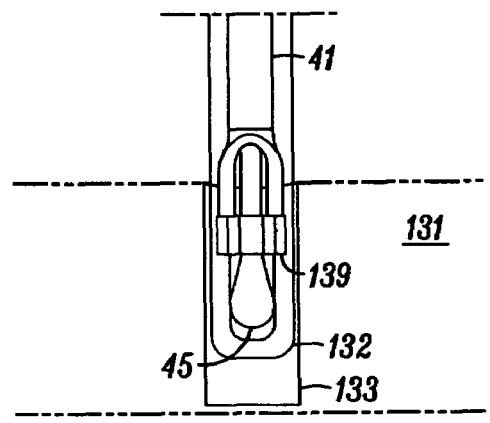
Figure 13C:
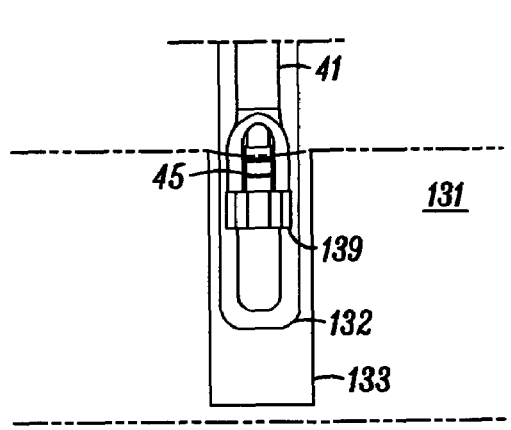
Figure 13D:
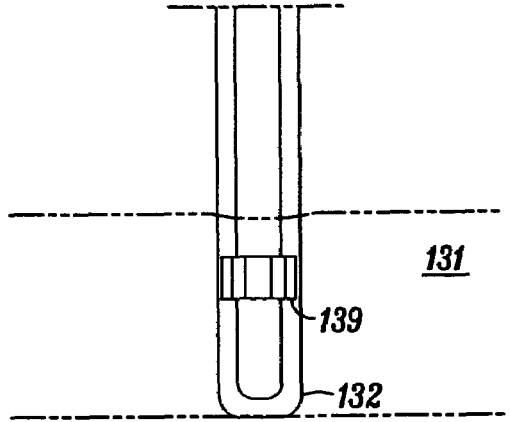
Figure 15A:
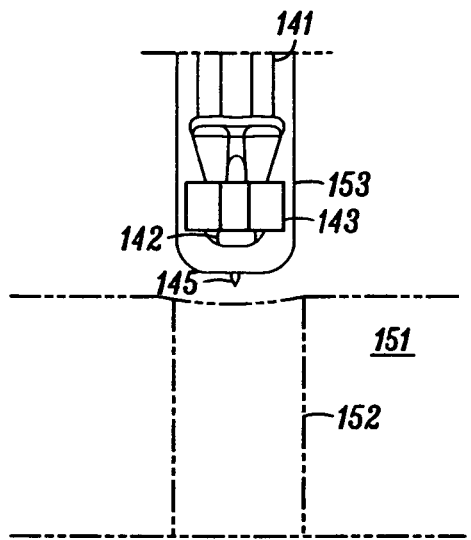
FIGS. 15A to 15D show side views showing the steps for securing a tendon to bone with a substantially non-cylindrical direct tendon anchor and the deployment instrument in FIGS. 14A to 14D.
Figure 15B:
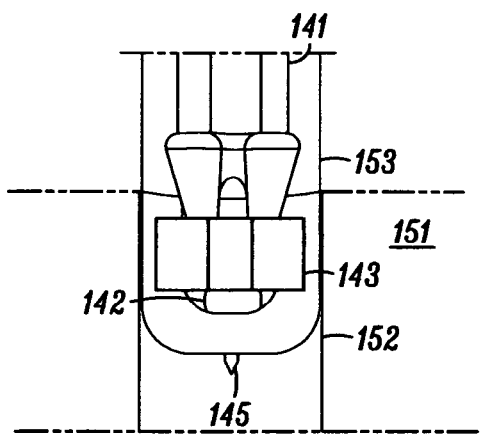
Figure 15C:
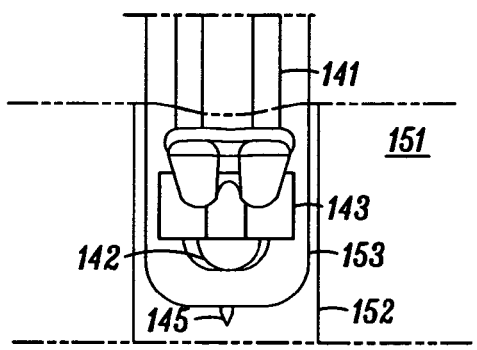
Figure 15D:
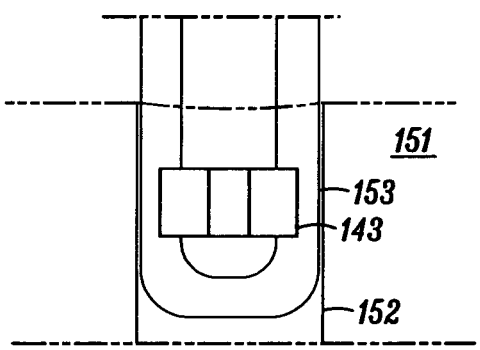

FIGS. 13A to 13D show exemplary steps for deploying and attaching a strand of tendon or graft within a drilled bone hole. The deployment instrument 41 of FIG. 4A is used to insert the looping strand 132 of tendon and the direct anchor 139 into a predrilled bone hole 133 in a bone 131. Once positioned, the dilator 45 is actuated, expanding the direct anchor 139 into engagement with the bone surface defined by the drilled hole 133 and compressing the tendon 132 against the bone. Once fully actuated, the deployment instrument 41 is removed, as shown in FIG. 13C, leaving the tendon 132, or graft, secured within the bone hole 133 via the direct anchor 139, as shown in FIG. 13D.

FIGS. 14A to 14D show two isometric views, a side view, and a side-sectional view, respectively, of an alternative deployment instrument embodiment 141 according to the present invention. This deployment instrument 141 uses an anvil 142 to support the direct anchor 143 while a shaft 144 incorporating an expansion transition is actuated and advanced relative to the direct anchor 143. Once actuated, the expansion shaft 144 is used to expand the direct anchor 143 into a radially enlarged orientation. Once fully expanded into the bone hole, the anvil 142 releases from the central lumen of the direct anchor 143 signaling full expansion of the direct anchor 143 thus completing attachment of the tendon(s) to the surface of the bone defined by the drilled hole. Until the direct anchor 143 is fully expanded, the anvil 142 supports the direct anchor 143 as the expansion shaft 144 continues to move axially further expanding the direct anchor 143.

This exemplary deployment instrument embodiment 141 further incorporates a tendon positioner 145 that aids in placement of the tendon into the bone hole. In the embodiment shown in FIGS. 14A to 14D, this positioner 145 is a needle tip that punctures into the tendon and holds the tendon while it and the direct anchor 143 are placed into the bone hole. Alternatively, the anvil 142 may incorporate a central lumen through which a clamp or snare can be manipulated to grasp the tendon. In this alternative grasping configuration, two opposing metal clamping ribbons are spring loaded to engage and compress around the tendon while grasping the tendon for placement. For the snare grasping mechanism, a single wire or ribbon is looped outside the central lumen. As the snare is advanced, the loop opens and as the snare is retracted, the loop compresses against the tendon placed within the snare opening. Once secured, the grasping mechanism is release from the tendon and removed from the bone hole.

FIGS. 15A to 15D show the exemplary deployment instrument 141 in FIGS. 14A to 14D used to place a segment of tendon 153 into a bone hole 152 and secure it by expanding the direct anchor 143 thereby engaging the anchor 143 to the surface of the bone 151 defined by the drilled hole 152 and compressing the tendon 153 against this surface to promote healing of the tendon 153 to the bone 151.

Figure 16A:
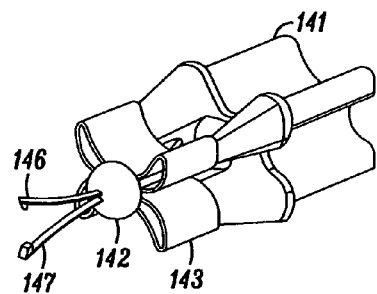
FIGS. 16A to 16D show isometrics views, side view, and end view of a substantially non-cylindrical direct tendon anchor with another exemplary deployment instrument embodiment according to the present invention.
Figure 16B:
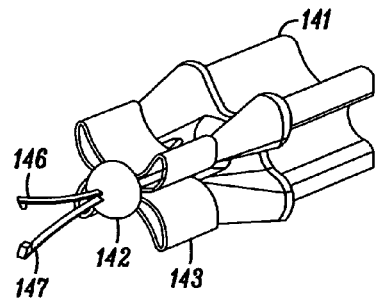
Figure 16C:
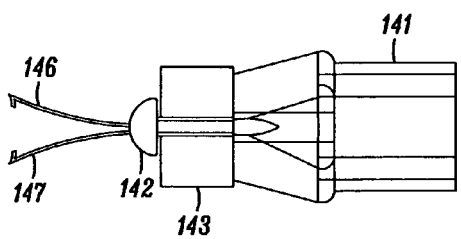
Figure 16D:
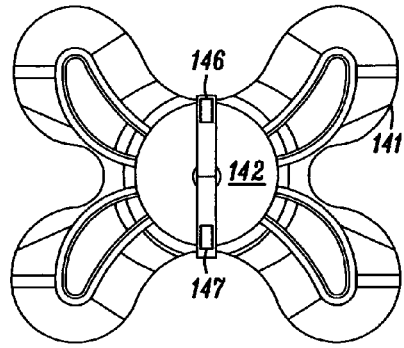
Figure 16E:
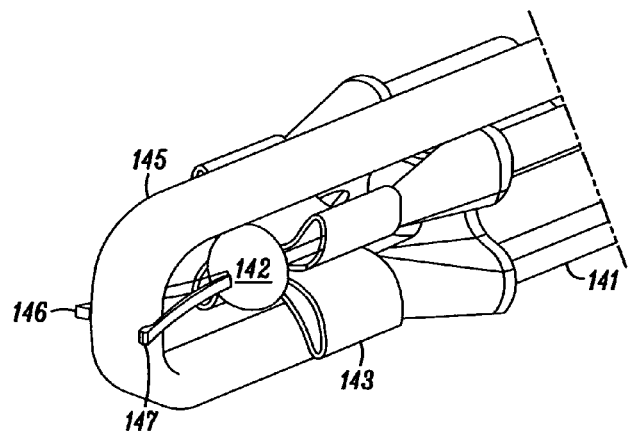
FIG. 16E shows an isometric view of the deployment instrument in FIGS. 16A to 16E with a tendon or graft engaged with the grasping mechanism.

FIGS. 16A to 16D show isometric views, a side view, and an end view, respectively, of the deployment instrument 141 in FIGS. 14A to 14D with the needle tip tendon engagement mechanism modified to a two ribbon wire 146 and 147 clamping mechanism. As the spring-loaded clamping mechanism 146 and 147 is advanced beyond the central lumen of the anvil 142 it expands into an enlarged opening between the two distal ends of the clamping mechanism 146 and 147. As the clamping mechanism 146 and 147 is placed over a tendon 145 or graft, as shown in FIG. 16E, the clamping mechanism 146 and 147 is retracted thereby clamping the tendon 145 and engaging it to enable positioning the clamp 146 and 147 along with the supported direct anchor 143 into the drilled bone hole for attachment.

FIGS. 17A to 17C show an isometric view, a side-sectional view, and a top view, respectively, of the substantially non-cylindrical direct anchor embodiment 71 in FIGS. 7 and 8 securing a segment of tendon 173 within a bone hole 172 of a bone 171. The tendon segment 173 loops around the distal end of the substantially non-cylindrical direct anchor 71 and fits within the opposing grooves. As the direct anchor 71 is expanded, using, for example, the deployment instrument embodiments shown above, the grooves are deflected outward compressing the tendon 173 against the surface of the bone 171 defined by the drilled hole 172, and engaging the butterfly extensions of the direct anchor 71 to the bone surface thereby attaching the tendon 173 within the bone hole 172.

FIGS. 18A to 18D show a side view, an isometric view, a side-sectional view, and a top view, respectively, of the substantially non-cylindrical direct anchor embodiment 71 shown in FIGS. 7 and 8 securing the free end of a tendon 183, or graft, within a bone hole 182 of a bone 181. The deployment instrument described above incorporates a grasping mechanism to grasp the free end of the tendon 183 and place the free end into the bone hole 182 such that the tendon 183 passes along one of the grooves in the direct anchor 71. Once positioned, the direct anchor 71 is expanded into the bone hole 182 to compress the tendon 183 against the surface of the bone 181 defined by the drilled hole and engage this surface with the extensions of the direct anchor.

Figure 19A:
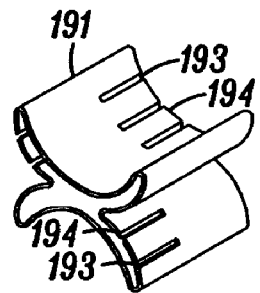
FIGS. 19A and 19B show isometric view and top view of an alternative substantially non-cylindrical direct tendon anchor embodiment in an unexpanded orientation.
Figure 19B:
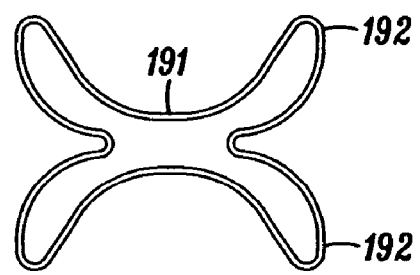

FIGS. 19A and 19B show an isometric and a top view of an alternative substantially non-cylindrical direct anchor embodiment 191 that incorporates "butterfly" extensions 192 that engage the surface of the bone defined by the drilled hole, and slots 193 that create flaps 194 that, once positioned and actuated, engage either the tendon and/or the surface of the bone defined by the drilled hole to increase the bond strength between the substantially non-cylindrical direct anchor 191 and the tendon to the bone.

Figure 19C:
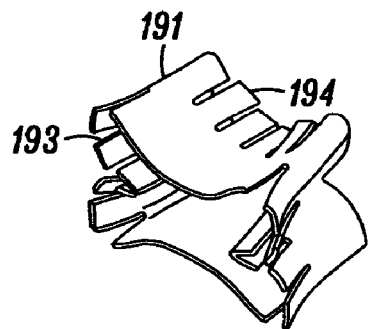
FIGS. 19C and 19D show isometric view and top view of the substantially non-cylindrical direct tendon anchor embodiment in FIGS. 19A and 19B in an expanded orientation.
Figure 19D:
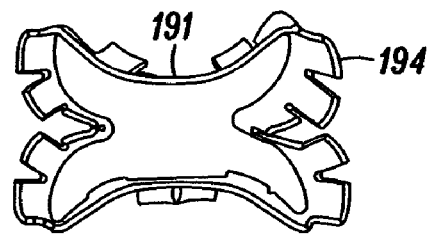

FIGS. 19C and 19D show an isometric view and a top view of the substantially non-cylindrical direct anchor embodiment 191 in FIGS. 19A and 19B in an expanded orientation with the substantially non-cylindrical direct anchor 191 fully deformed to compress tendon against the surface of the bone defined by the drilled hole and engage the bone anchor to that surface.

FIGS. 20A and 20B show isometric views of two alternative direct anchor embodiments 201 and 205 that incorporate a "clover leaf" proximal end 202 transitioning to a cone distal end 203. The embodiment of FIG. 20A further incorporates loops 204 that are either connected to the distal end 203 or pass through the central lumen where they connect to another component of the anchor 201 or are incorporated as one or more snares to the deployment instrument, previously described.

FIGS. 20C and 20D show an isometric view and a top view of the direct anchor embodiment 205 of FIG. 20B in an unexpanded orientation. FIGS. 20E and 20F show an isometric view and a top view of the direct anchor embodiment 205 in FIGS. 20B to 20D in an expanded orientation. The proximal end 202 of the embodiment in FIG. 20A would expand similar to that for the embodiment shown in FIGS. 20E and 20F. As the direct anchor 205 expands, the inner grooves 208 are deflected outward whereby they partially straighten into a larger radius of curvature, as shown in FIGS. 20D and 20F.

Correspondingly, the "clover leaf" extensions 209 are radially expanded into engagement with the surface of the bone defined by the drilled hold. These extensions 209 also open up while the direct anchor 205 is deployed, however their pre-shaped radii of curvature are less than that for the grooves 208; therefore, any expansion of the direct anchor 205 straightens the grooves 208 before the extensions 209 open up. That way, the extensions 209 maintain their ability to engage the bone surface defined by the drilled hole.

FIGS. 21A to 21D show a side-sectional view, a cross-sectional view oriented away from the bone axis, a cross-sectional view oriented towards the bone axis, and a top view, respectively, of the direct anchor 205 in FIG. 20B to 20F with four strands 213 of tendon supported by the grooves 208 of the direct anchor 205. The four strand 213 engagement is common with the hamstring ACL reconstruction at a bone hole 212 in the tibial 211 attachment side. It should be noted that this direct anchor embodiment 205 may alternatively be used to secure one or two strands of tendon 213, or graft during double tendon strand or sliding anchor techniques.

FIGS. 22A and 22B, and 22C and 22D show two substantially non-cylindrical direct anchor embodiments 221 capable of being used during double tendon strand or sliding anchor techniques described above, as well as rotator cuff repair and suturing the tendon to the implant techniques. This substantially non-cylindrical direct anchor embodiment 221 incorporates offset openings 222 through which one or more suture strands can be inserted.

Figure 22A:
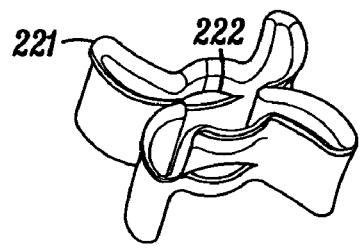
FIGS. 22A and 22B show isometric views of a substantially non-cylindrical suture anchor embodiment according to the present invention.
Figure 22B:
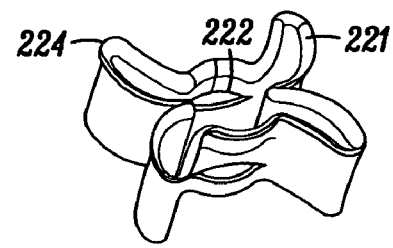
Figure 22C:
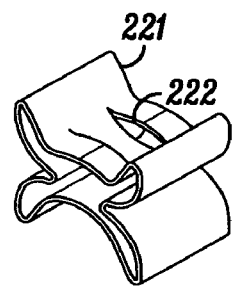
FIGS. 22C and 22D show isometric view and top view of an alternative substantially non-cylindrical suture anchor embodiment in an unexpanded orientation.
Figure 22D:
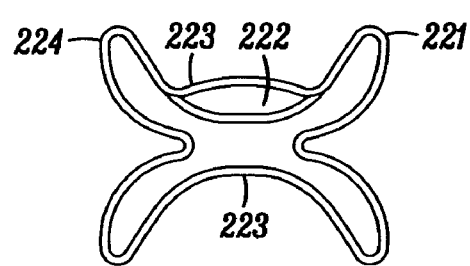
Figure 22E:
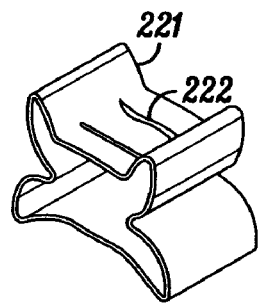
FIGS. 22E and 22F show isometric view and top view of the substantially non-cylindrical suture anchor embodiment in FIGS. 22C and 22D in an expanded orientation.
Figure 22F:
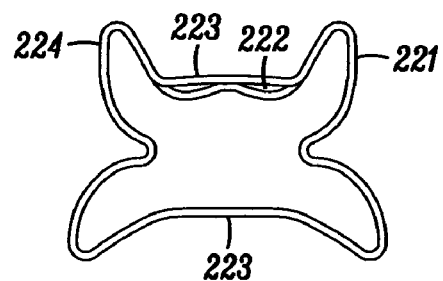

Once the suture is inserted and the direct anchor 221 is expanded, as shown in FIGS. 22E and 22F, the suture is secured to the direct anchor 221 as the openings 222 are deformed closed locking the suture in place. Meanwhile the grooves 223 are expanded outward thereby compressing any tendon positioned along the groove 222 against the surface of the bone defined by the drilled hole. In addition, the "butterfly" extensions 224 are expanded radially outward into engagement with this bone surface thereby securing the direct anchor 221 to the bone.

Figure 23A:
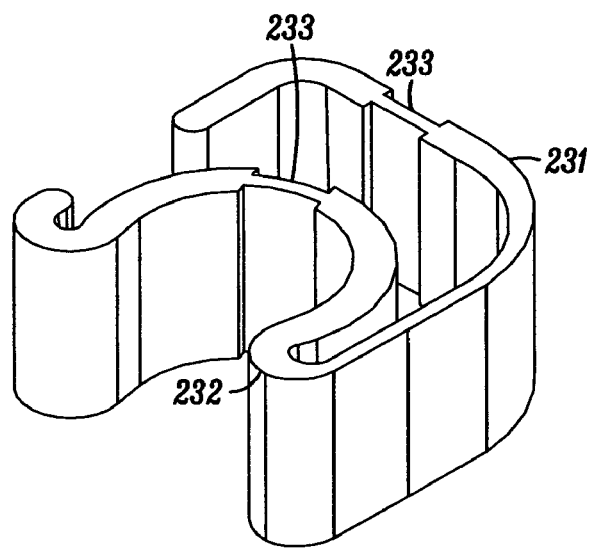
FIGS. 23A to 23C an show isometric view, bottom view and top view of an alternative substantially non-cylindrical direct tendon anchor embodiment according to the present invention.
Figures 23B, 23C:
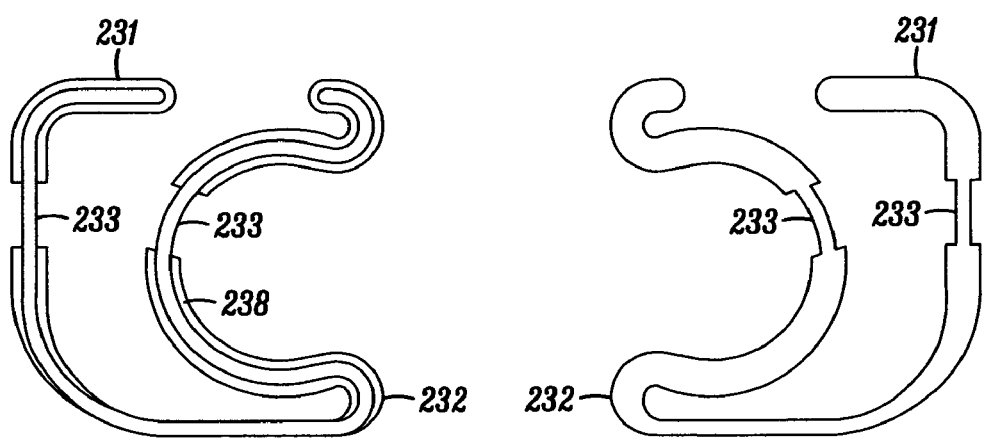

FIGS. 23A to 23C show an isometric view, a bottom view and a top view, respectively, of an alternative substantially non-cylindrical direct anchor embodiment 231 according to the present invention. In this embodiment, the substantially non-cylindrical direct anchor 231 incorporates a flex region 232 along which the substantially non-cylindrical direct anchor 231 (in this case fabricated from a resilient elastic member) can be compressed into a small diameter for insertion into the bone. Once positioned, this direct anchor 231 is released to expand towards its preformed configuration where it locks to the bone surface defined by the drilled hole and compresses the tendon against that surface. It should be noted that the substantially non-cylindrical direct anchor 231 may alternatively be deformable and manually expanded, via actuation with a deployment clamp, into an enlarged, deformed orientation whereby the direct anchor 231 engages the bone surface. Two notches 233 are incorporated in the direct anchor 231 for a clamp to temporarily engage the direct anchor 231 and enable manipulating the direct anchor 231 into a compressed or enlarged orientation. The cross-section of the direct anchor 231 resembles the cross-section of a cone such that the proximal wider edge can engage the surface of the bone defined by the drilled hole along the periphery of the direct anchor.

FIGS. 24A to 24D show two side views, a side-sectional view, and a top view, respectively, of the substantially non-cylindrical direct anchor embodiment 231 in FIGS. 23A to 23C securing the free end of a tendon 243, or graft, within a bone hole 242 of a bone 241. This embodiment 231 enables clamping the tendon 243, or graft, in the central opening 238 defined by the "C" link and the outer link of the integrated direct anchor 231. The clamp deployment mechanism is used to enlarge this central opening 238 for positioning around the free end of the tendon 243 such that once positioned, the clamp is relaxed compressing the tendon 243 between the opposing links thereby engaging the tendon 243 to the direct anchor 231 for placement. Next the tendon 243 is positioned within the lumen 238 of the "C" link such that it can be compressed against the bone surface defined by the drilled hole 242 once deployed.

FIGS. 25A to 25F show two top views, an isometric view, a cross-sectional view, a side view, and a side-sectional view, respectively, of the substantially non-cylindrical direct anchor embodiment 231 in FIGS. 23A to 23D securing an in-line segment of tendon 253 within a bone hole 252 of a bone 251. As described above, this substantially non-cylindrical direct anchor embodiment 231 is enlarged to engage a segment of tendon 253 such that the tendon 253 loops around the distal end of the direct anchor 231. After engaging the tendon 253, the substantially non-cylindrical direct anchor 231 is compressed into a small diameter for positioning into a bone hole 252. Once positioned, the substantially non-cylindrical direct anchor 231 is released or manually enlarged to secure the substantially non-cylindrical direct anchor 231 to the surface of the bone 251 defined by the drilled hole 252 and compress the tendon 253 against that surface.

Figure 26A:
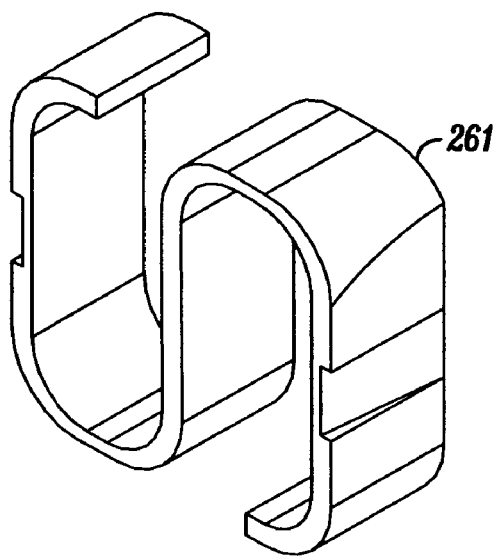
FIGS. 26A to 26C show an isometric view, bottom view, and top view of an alternative direct tendon anchor embodiment of the invention.
Figures 26B, 26C:
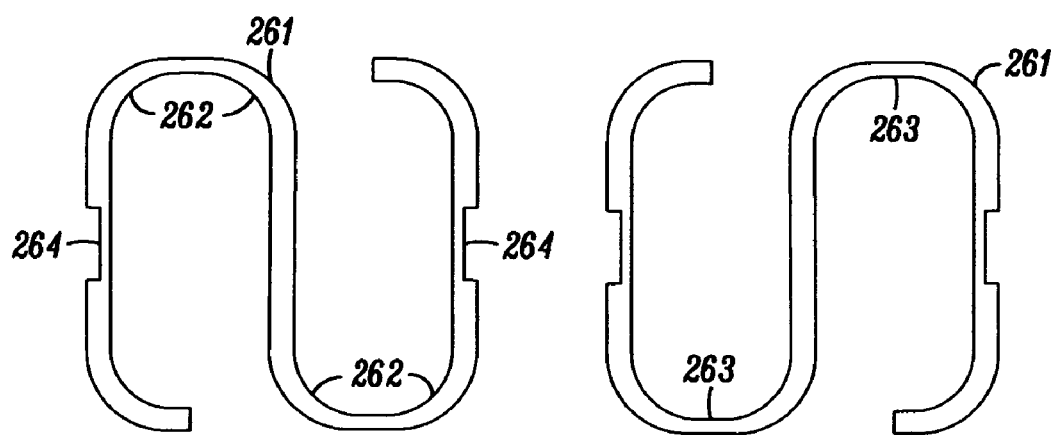
Figure 27A:
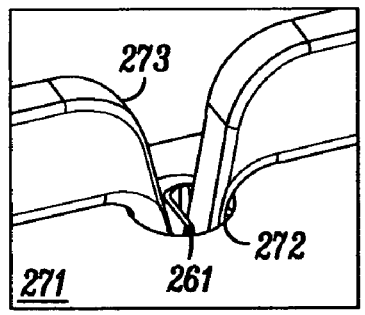
FIGS. 27A to 27F show isometric view, side view, isometric shaded view, side-sectional view, top view, and cross-sectional view of the direct tendon anchor embodiment in FIGS. 26A to 26D securing a segment of tendon to bone.
Figure 27B:
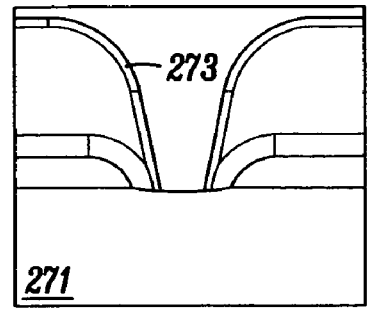
Figure 27C:
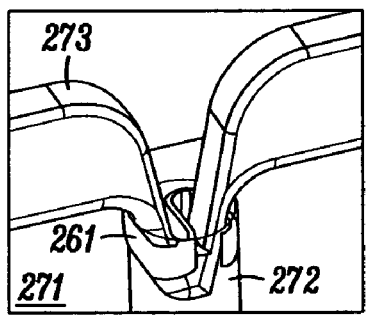
Figure 27D:
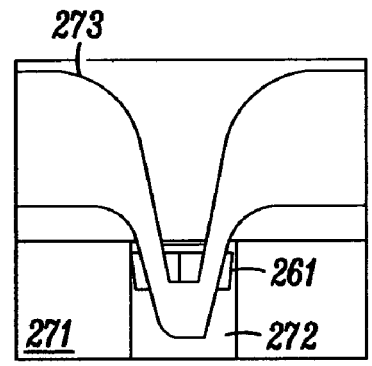
Figure 27E:
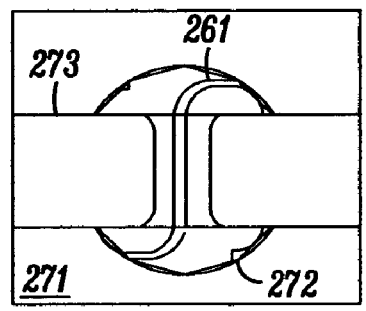
Figure 27F:
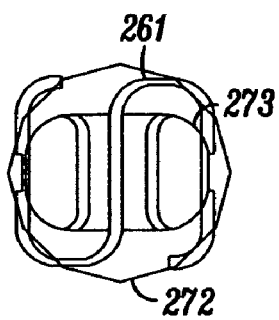

FIGS. 26A to 26C show an isometric view, a bottom view, and a top view, respectively, of an alternative direct anchor embodiment 261. This embodiment also incorporates flex regions 262 along which the direct anchor 261 can be compressed or enlarged. The direct anchor 261 incorporates openings 263 through which tendon can be engaged during actuation of the direct anchor 261. In addition, opposing notches 264 along the outer "S" links are configured for a clamp to engage the "S" direct anchor 261 for compressing or expanding the direct anchor 261.

FIGS. 27A to 27F show an isometric view, a side view, a shaded isometric view, a side-sectional view, a top view, a cross-sectional view, respectively, of the direct anchor embodiment 261 shown in FIGS. 26A to 26C with a tendon 273 looped around the distal link of the "S" direct anchor 261 positioned in a bone hole 272 of a bone 271.

Figure 28A:
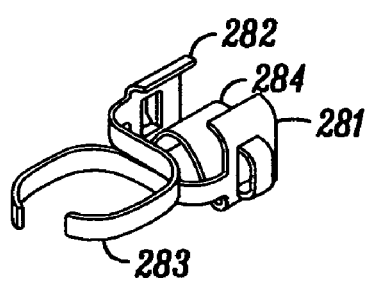
FIGS. 28A and 28B show isometric view and side view of an alternative substantially non-cylindrical direct tendon anchor embodiment according to the present invention.
Figure 28B:
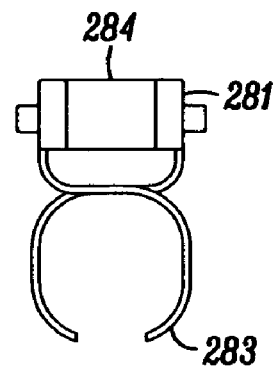

FIGS. 28A and 28B show an isometric view and a side view of another exemplary substantially non-cylindrical direct anchor embodiment 281 that may also function as a clamp. This substantially non-cylindrical direct anchor embodiment 281 incorporates opposing engagement ears 282 through which a deployment actuator can engage the base of the direct anchor 281 for manipulation. In addition, clamp legs 283 are incorporated in the substantially non-cylindrical direct anchor 281 for engaging the tendon. This substantially non-cylindrical direct anchor 281 further incorporates a central flex region along which the base 284 of the direct anchor 281 can be compressed or expanded, thereby expanding or compressing the clamp legs 283.

Figure 28C:
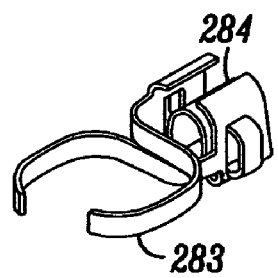
FIGS. 28C and 28D show isometric view and side view of the substantially non-cylindrical direct tendon anchor embodiment in FIGS. 28A and 28B in an open orientation for grasping the tendon according to the present invention.
Figure 28D:
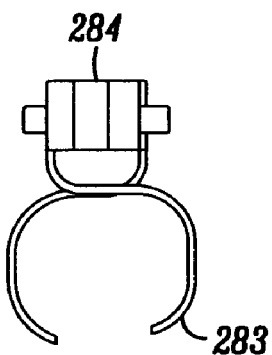
Figure 28E:
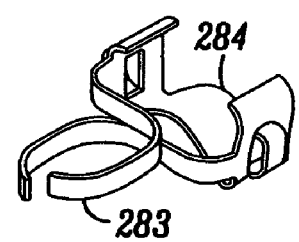
FIGS. 28E & 28F show isometric view and side view of the substantially non-cylindrical direct tendon anchor embodiment in FIGS. 28A and 28B in a deployed orientation for securing the tendon to bone.
Figure 28F:
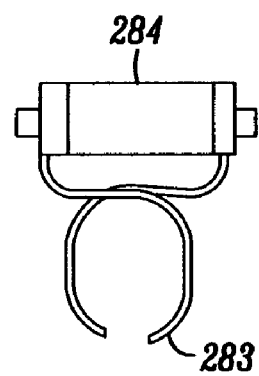
Figure 29A:
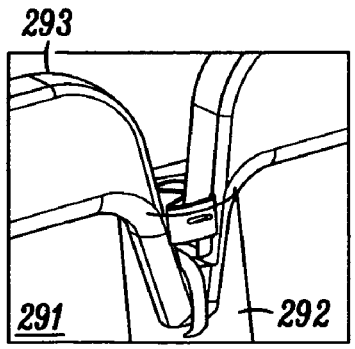
FIGS. 29A to 29F show isometric views, top views, cross-sectional view, and side-sectional view of the substantially non-cylindrical direct anchor embodiment in FIGS. 28A to 28F in a deployed orientation securing a tendon to bone.
Figure 29B:
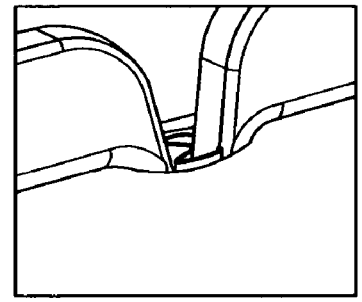
Figure 29C:
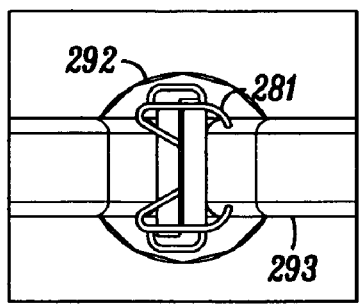
Figure 29D:
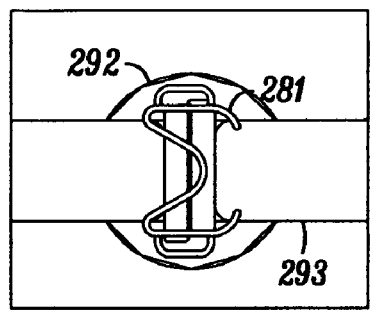
Figure 29E:
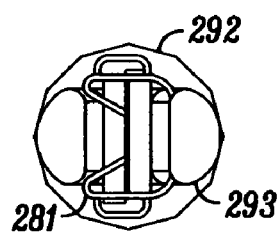
Figure 29F:
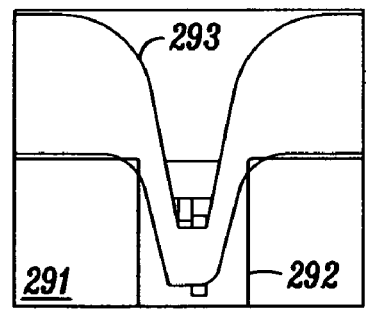
Figure 31A:
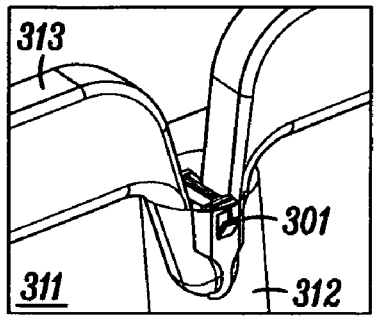
FIGS. 31A to 31F show isometric views, side view, side-sectional view, top view, and cross-sectional view of the substantially non-cylindrical direct anchor embodiment in FIGS. 30A to 30F securing a tendon to bone.
Figure 31B:
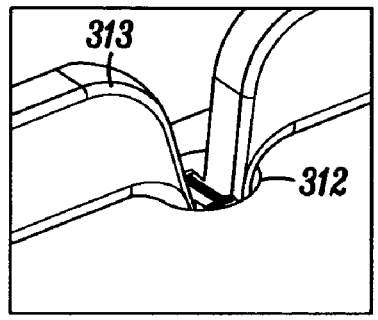
Figure 31C:
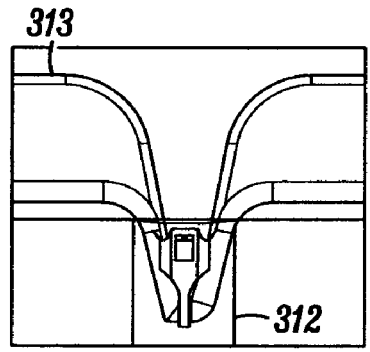
Figure 31D:
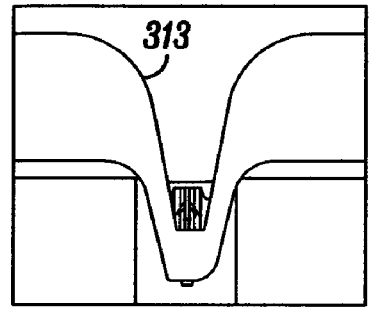
Figure 31E:
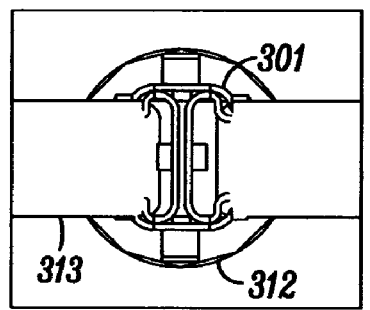
Figure 31F:
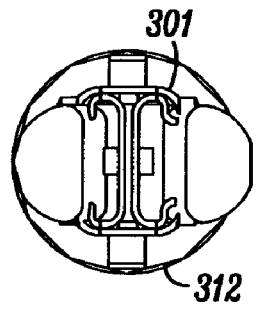
Figure 33A:
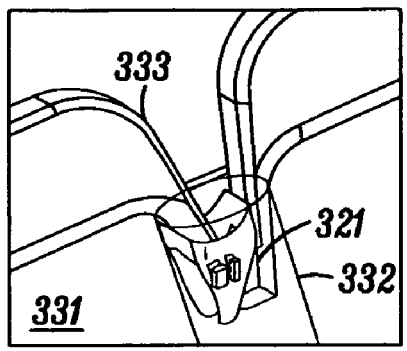
FIGS. 33A to 33F show isometric views, side view, side-sectional view, top view, and cross-sectional view of the direct tendon anchor embodiment in FIGS. 32A to 32C securing a tendon to bone.
Figure 33B:
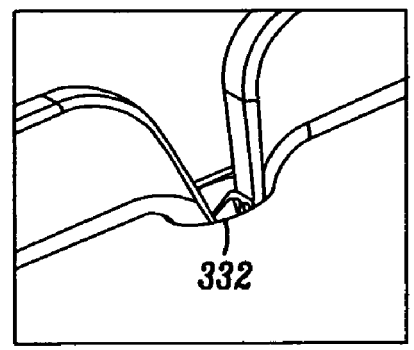
Figure 33C:
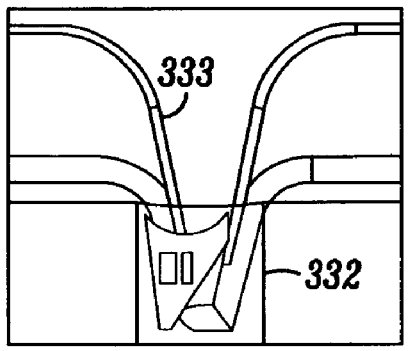
Figure 33D:
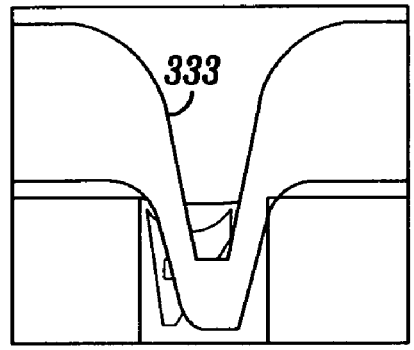
Figure 33E:
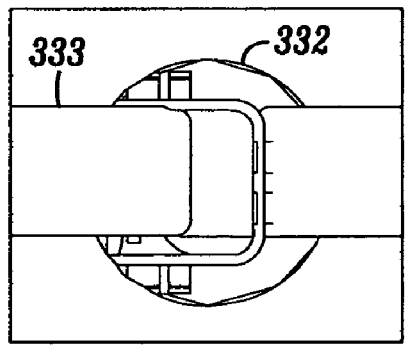
Figure 33F:
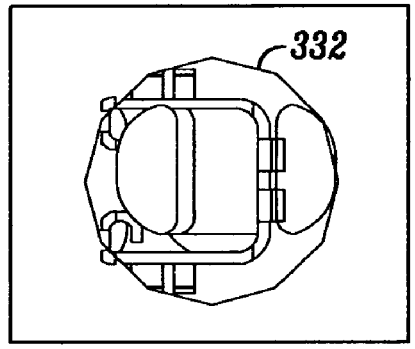
Figure 34A:
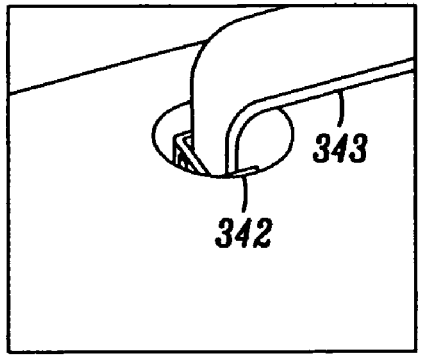
FIGS. 34A to 34D show isometric view, top view, side view, and side-sectional view of an alternative substantially non-cylindrical direct tendon anchor embodiment securing the end of a tendon to bone.
Figure 34B:
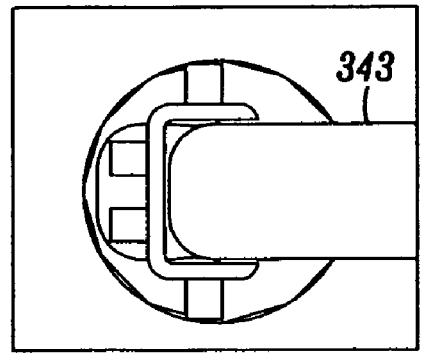
Figure 34C:
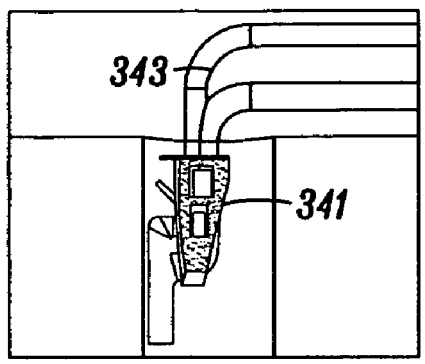
Figure 34D:
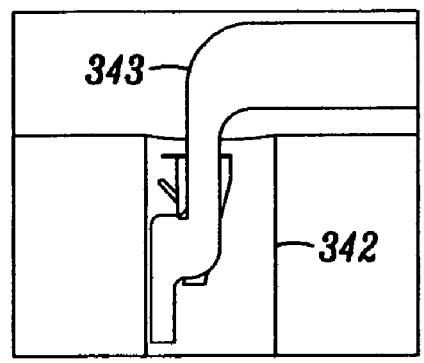
Figure 35A:
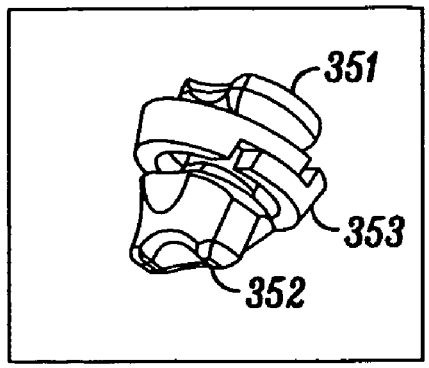
FIGS. 35A to 35D show isometric views, side view, and top view of an exemplary multiple component tendon anchor embodiment according to the present invention.
Figure 35B:
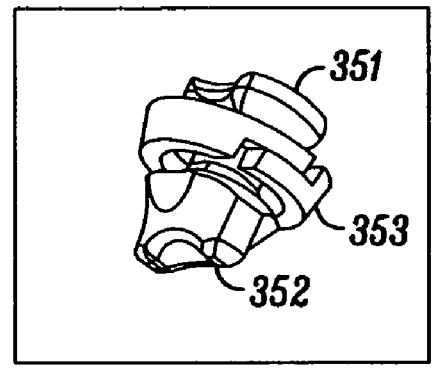
Figure 35C:
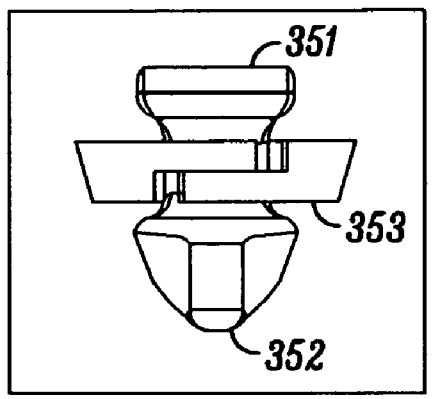
Figure 35D:
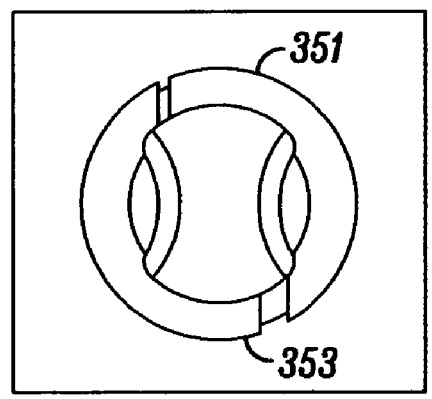

FIGS. 28C and 28D show the substantially non-cylindrical direct anchor embodiment 281 in FIGS. 28A and 28B in a compressed orientation where the base is actuated into a compressed orientation such that the clamp legs 283 enlarge for grasping a tendon. Once the tendon is grasped and the substantially non-cylindrical direct anchor 281 and engaged tendon are positioned into a bone hole, the base 284 is expanded, as shown in FIGS. 28E and 28F. Once the substantially non-cylindrical direct anchor 281 is allowed to expand (e.g., a resilient anchor released to return towards its preformed configuration) or deformed into an expanded orientation the direct anchor 281 increases compression of the tendon securing the tendon to the direct anchor 281 and the base 284 expands into engagement with the surface of the bone defined by the drilled hole.

FIGS. 29A to 29F show two isometric views, two top views, a cross-sectional view, and a side-sectional view, respectively, of the substantially non-cylindrical direct anchor embodiment 281 in FIGS. 28A to 28F securing a segment of tendon 293, or graft, within a bone hole 292 of a bone 291.

FIGS. 30A to 30C show an isometric view, a top view, and a side view, respectively, of an alternative substantially non-cylindrical direct anchor embodiment 301 according to the present invention. This substantially non-cylindrical direct anchor 301 incorporates a central opening 302 through which a dilation mechanism can be advanced to expand the direct anchor 301 into engagement with the surface of the bone defined by the drilled hole. Tabs 303 and 304 are also included in the direct anchor 301 to ensure attachment of the tendon to the anchor 301 and the anchor 301 to the bone hole. The central tabs 303 prevent movement of the tendon relative to the substantially non-cylindrical direct anchor 301 once positioned and expanded into engagement. The reverse tabs 304 prevent dislodgement of the substantially non-cylindrical direct anchor 301 from the bone hole once positioned and secured. Clamp legs 308 define an opening into which the tendon can be placed and supported during positioning of the tendon and direct anchor into the bone hole. Grooves 309 provide openings into which tendon strands can be placed and compressed against the surface of the bone defined by the drilled hole once the substantially non-cylindrical direct anchor 301 is expanded with the deployment instrument.

FIGS. 30D to 30F show an isometric view, a top view, and a side view, respectively, of the embodiment shown in FIGS. 30A to 30C in an expanded orientation.

FIGS. 31A to 31F show two isometric views, a side view, a side-sectional view, a top view, and a cross-sectional view, respectively, of the substantially non-cylindrical direct anchor embodiment 301 shown in FIGS. 30A to 30F securing a segment of tendon 313 within a bone hole 312 of a bone 311.

FIGS. 32A to 32C show an isometric view, a side view, and a top view of another exemplary direct anchor embodiment 321 for securing a segment of tendon within a bone hole. Tabs 322 extending from the direct anchor 321 engage the surface of the bone defined by the drilled hole to secure the tendon and the direct anchor 321 within the bone hole. FIGS. 33A to 33F show two isometric views, a side view, a side-sectional view, a top view, and a cross-sectional view, respectively, of the direct anchor 321 shown in FIGS. 32A to 32C securing a segment of tendon 333 within a bone hole 332 of a bone 331.

FIGS. 34A to 34D show an isometric view, a top view, a side view, and a side-sectional view of another substantially non-cylindrical direct anchor 341 securing a free end of tendon 343 within a bone hole 342 of a bone 341.

FIGS. 35A to 35D show two isometric views, a side view, and a top view of an exemplary multiple component direct anchor embodiment 351 according to the present invention. This multiple component direct anchor 351 incorporates a central tip 352 around which the tendon loops and a proximal, radially expanding base 353 that expands as tension is applied to the central tip 352 thereby further expanding into engagement with the surface of bone defined by the drilled hole. Therefore, as tension is applied to the tendon, the central tip 352 is retracted thereby enlarging the diameter of the proximal base 353 which further engages the bone surface ensuring the tendon does not pull free from the bone hole. The proximal base 353 can consist of two mating pieces that are free moving, slide radially relative to each other, are hinged at one end with the other free to move so the base can radially expand, or otherwise define a radially expansion mechanism that enlarges in diameter as the central tip is retracted.

Figure 36A:
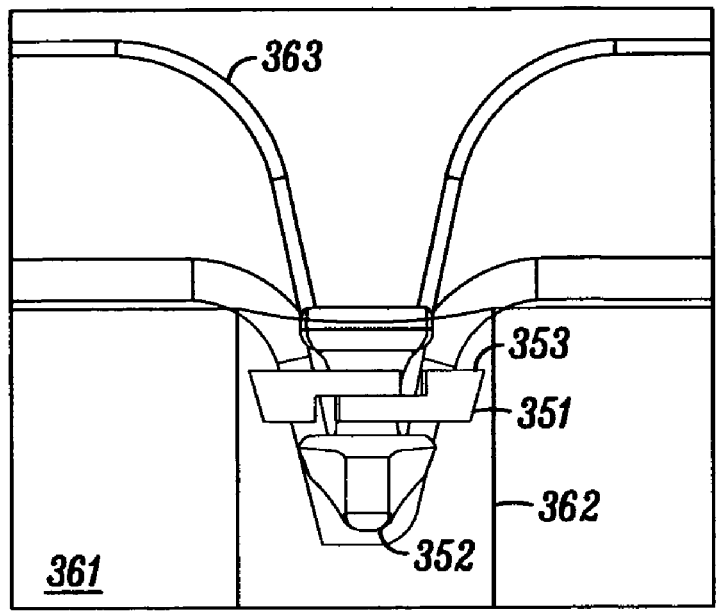
FIGS. 36A and 36B show side view and top view of the multiple component tendon anchor embodiment in FIGS. 35A to 35D securing a tendon to bone.
Figure 36B:
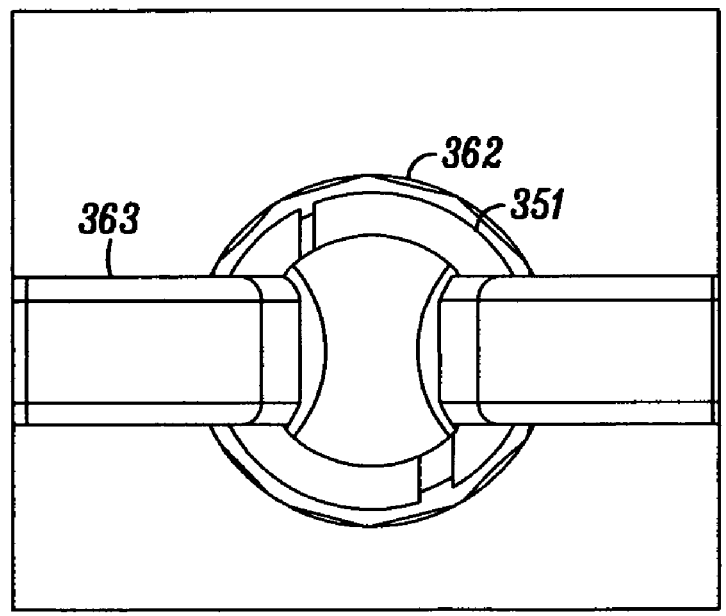
Figure 37A:
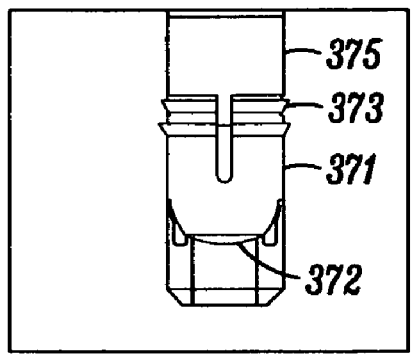
FIGS. 37A to 37D show front view, isometric view, side view, and end view of an alternative multiple component tendon anchor embodiment and an exemplary deployment instrument embodiment according to the present invention.
Figure 37B:
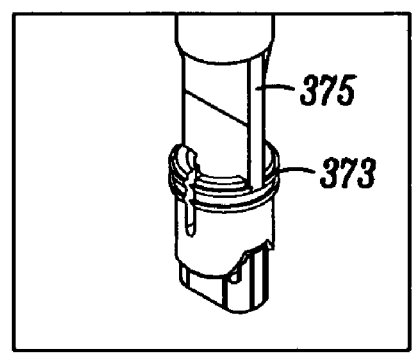
Figure 37C:
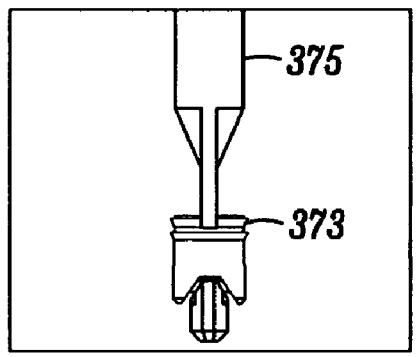
Figure 37D:
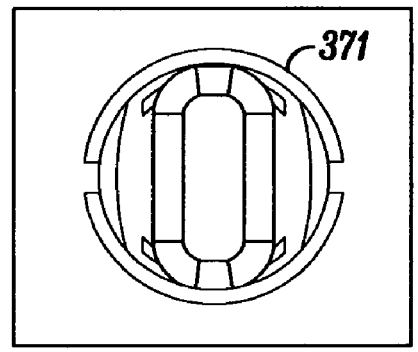

FIGS. 36A and 36B show a side view and a top view of the direct anchor embodiment 351 shown in FIGS. 35A to 35D securing a segment of tendon 363 within a bone hole 362 of a bone 361. As shown in FIGS. 36A and 36B, the tendon 363 loops inside the proximal base 353 and around the central tip 352 thereby securing the tendon 363 to the direct anchor 351 and ensuring that any tension on the tendon 363 causes the proximal base 353 to enlarge thus increasing the engagement of the direct anchor 351 to the bone 361 and ensuring integrity of the bone 361 to anchor 353 to tendon 363 bond.

FIGS. 37A to 37D show a front view, an isometric view, a side view, and an end view of an alternative multiple component direct anchor embodiment 371 with a deployment instrument 375. As described above for the embodiment shown in FIGS. 35A to 35D, the tendon loops around the central tip after passing within the lumen of the base. The deployment instrument 375 engages the proximal base and defines space along which the tendon can pass.

Figure 38A:
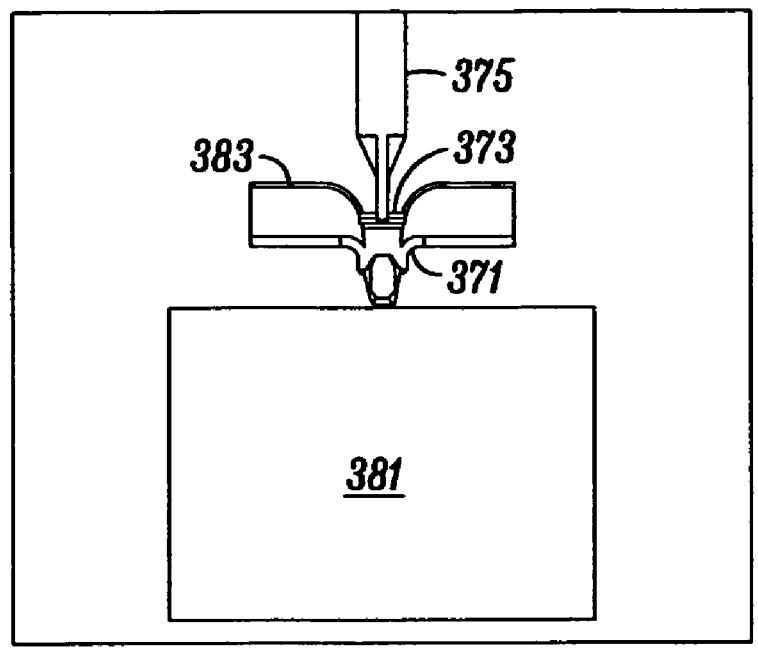
FIGS. 38A and 38B show side view and isometric view of the multiple component tendon anchor embodiment in FIGS. 37A to 37D positioning a tendon into a drilled bone hole.
Figure 38B:
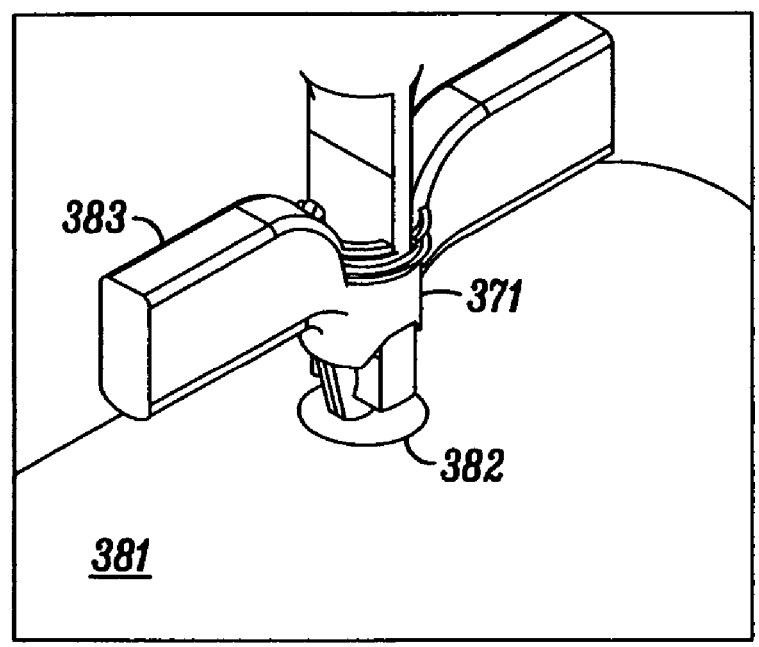
Figure 39A:
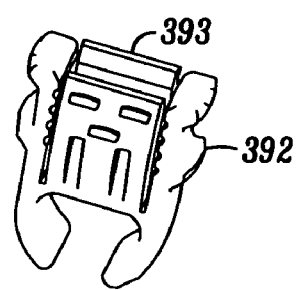
FIGS. 39A to 39F show isometric views, side view, and top view of a substantially non-cylindrical multiple component tendon anchor embodiment according to the present invention.
Figure 39B:
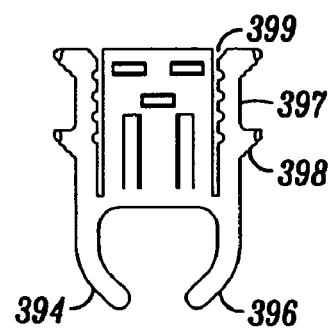
Figure 39C:
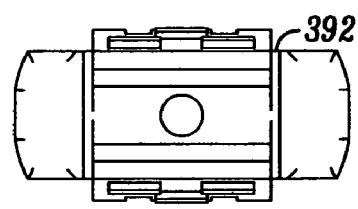
Figure 39D:
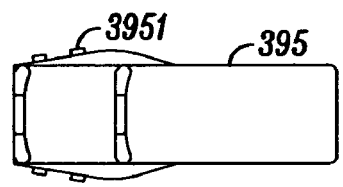
Figure 39E:
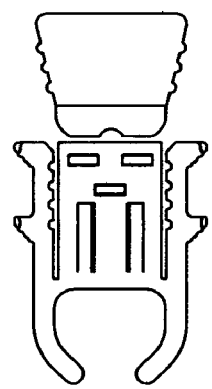
Figure 39F:
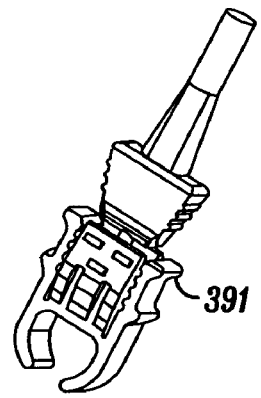
Figure 40A:
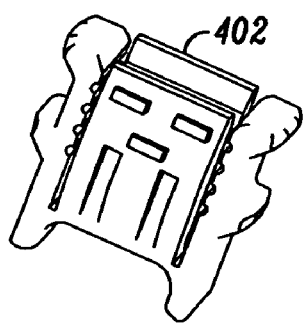
FIGS. 40A to 40F show isometric views, side view, and top view of a substantially non-cylindrical multiple component tendon anchor embodiment according to the present invention.
Figure 40B:
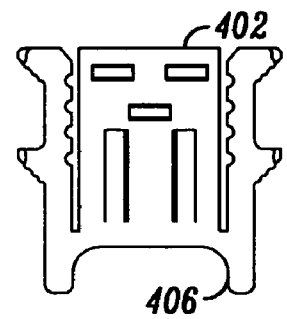
Figure 40C:
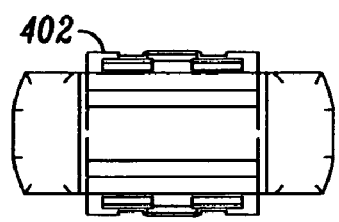
Figure 40D:
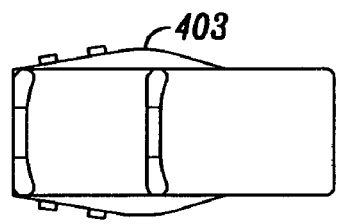
Figure 40E:
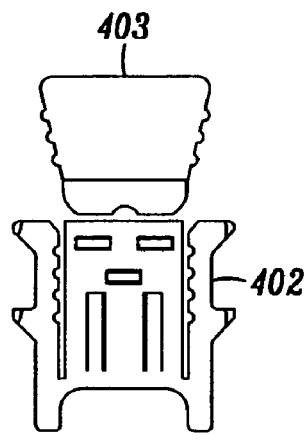
Figure 40F:
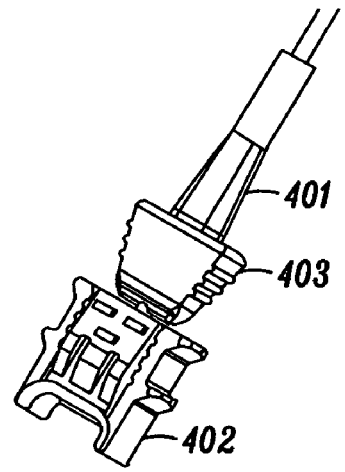
Figure 41A:
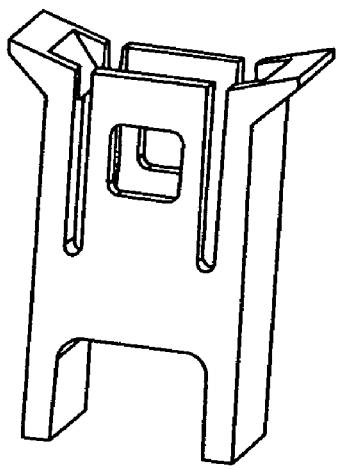
FIGS. 41A to 41D show isometric views, side view, and top view of a substantially non-cylindrical multiple component tendon anchor embodiment according to the present invention.
Figure 41B:
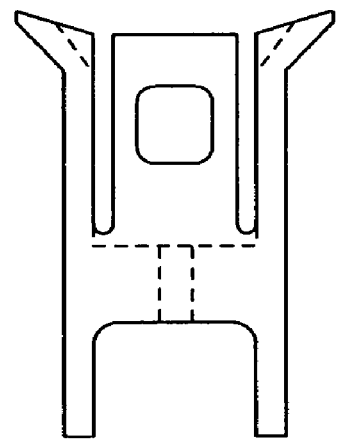
Figure 41C:
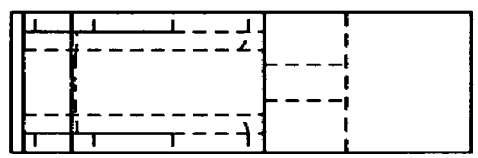
Figure 41D:
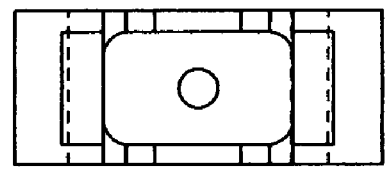
Figure 43A:
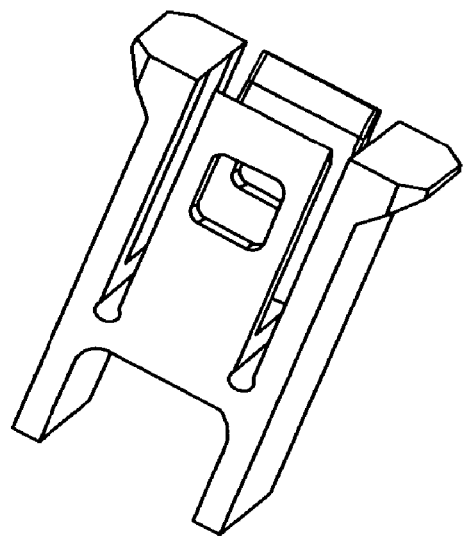
FIGS. 43A to 43D show isometric views, side view, and top view of a substantially non-cylindrical multiple component tendon anchor embodiment according to the present invention.
Figure 43B:
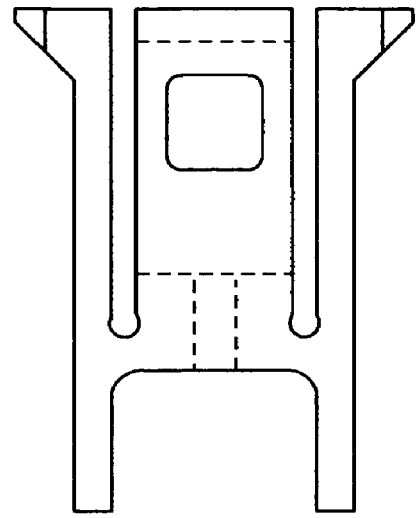
Figure 43C:
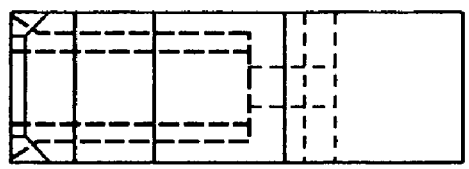
Figure 43D:
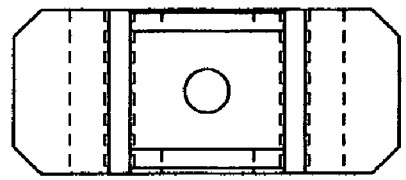
Figure 44A:
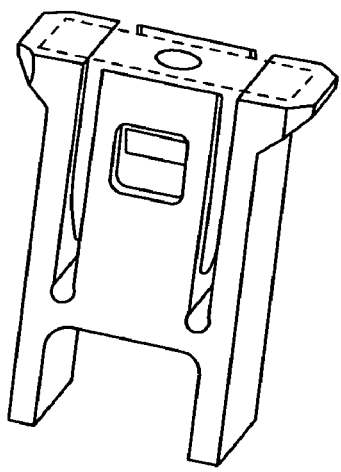
FIGS. 44A to 44D show isometric views, side view, and top view of a substantially non-cylindrical multiple component tendon anchor embodiment according to the present invention.
Figure 44B:
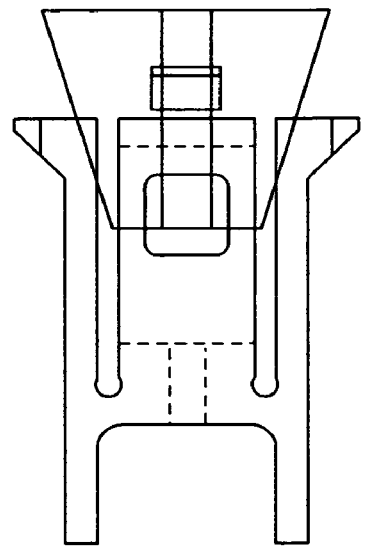
Figure 44C:
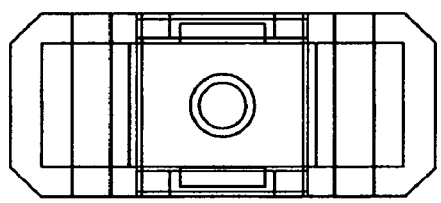
Figure 44D:
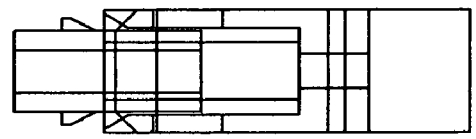

FIGS. 38A and 38B show a side view and an isometric view of the deployment of the direct anchor embodiment 371 in FIGS. 37A to 37D. With a tendon segment 383 or free end secured to the multiple direct anchor 371 by looping the tendon 383 around the central tip 372 and within the proximal base 373, the deployment instrument 375 is used to position the tendon 383 and direct anchor 371, in an unstressed low profile orientation, into the bone hole 382. Once positioned, tension is applied either to the central tip 372 or to the tendon 383 thereby enlarging the proximal base 373 into engagement with the surface of the bone 381 defined by the drilled hole 382. In this expanded orientation, the proximal base 373 secures the direct anchor 371 and the attached tendon 383 within the bone hole 382 such that any additional tension applied to the tendon 383 increases the engagement between the multiple component direct anchor 371 and the bone 381.

FIGS. 39A to 39F show isometric views, side view, and top view of an exemplary substantially non-cylindrical, multiple component tendon anchor embodiment 391 according to the present invention. In this embodiment there are two implant components: (a) an outer anchor 392 and (b) an inner wedge piece 395. The outer anchor component's four side walls (arms) 393 can be deflected both inward and outward during deployment. Inward deflection may be allowed to make advancement of the device 391 into the bone hole easier, while outward deflection will anchor the implant 391 to the bone. The center arms 394 are in direct contact with a tendon which is aligned and looped around the distal end of the implant 391. The flattened or curvilinear shape of the center arms 394 is designed to optimize the implant to tendon contact area, which in turn increases the tendon to bone contact area. The extended distal elements (anchor claw) 396 are included to aid in the alignment of the tendon. The lateral arms 397 directly contact the bone surface and can have various protrusions or extensions 398 that anchor the implant 391 into the bone. The slots 399 between each of the arms 397 allow each arm to function and deflect independently to the adjacent arm. Moreover, these slots 399 allow for the adjustable expansion of the implant.

The wedge piece component 395 of the implant includes a taper design with tabs 3951 that engage the outer anchor component 392 when inserted and advanced. The wedge shape of the component 395 expands the outer anchor arms 397 radially outward as it is advanced distally, simultaneously pushing the tendon against the bone surface and anchoring the implant 391 to the bone by expanding the lateral walls 397 into the bone. Procedurally, the tendon is looped around and positioned over the implant 391. After the tendon has been engaged, the tendon—implant is advanced through the bone hole. Once in position, the anchor 391 is deployed by advancing the wedge 395 to secure the anchor 391 to the bone surface and compress the tendon to the bone surface as defined by the bone hole.

FIG. 40A to 40F show isometric views, side view, and top view of an exemplary substantially non-cylindrical, multiple component tendon anchor embodiment 401 according to the present invention, including an outer anchor 402 and a wedge 403. This embodiment 401 is a derivative of that described in FIGS. 39A to 39F with a smaller variation in the distal anchor claw 406 used for positioning and alignment of the tendon. Variation in the position, shape, and number of tabs or facets on the arms of the implant can be used to optimize the anchoring of the implant to the bone as well as improve the tendon to bone surface contact. The profile of the implant arms may also be an embodiment that has an "I" beam cross section as compared to a rectangular cross section shown. This "I" beam shape would allow a deeper center channel for the positioning and alignment of the tendon as well as provide a larger surface area contact between the bone and the anchor surface. In addition, the lateral arms of the implant need not be limited to rectangular cross section, but other embodiments may also have a curvilinear shape similar to that of the bone hole. The intention of this curvilinear shape variation would be to increase the surface area contact of the bone to the implant.

FIGS. 41-44 show different variations of the outer implant. Variations in the angle and shape of the anchor arm slot can be achieved with different embodiments. In these embodiments, the angle of the slot will affect the stress distribution along the outer anchor and at the base of the arms of the outer anchor. Various embodiments can include different slot angles to minimize the stresses on the implant during expansion and well as pullout. By orienting the slot angles or tapering the slots, one can optimize the axial force transfer of the implant, resulting in potentially higher pullout strength by reducing the failure of the system due to fracture of the anchor implant. The embodiments included in this application include optimization of design with respect to the thickness of the arms, the expandability of the implant, the strength of fixation required for the anchor, the fracture resistance of the anchor, manufacturability and overall size.

Figure 45A:
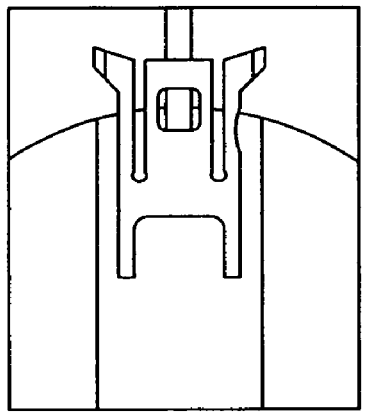
FIGS. 45A to 45D show side view of anchor delivery, inner wedge advancement and deployment of the substantially non-cylindrical tendon anchoring embodiment shown in FIGS. 44A to 44D.
Figure 45B:
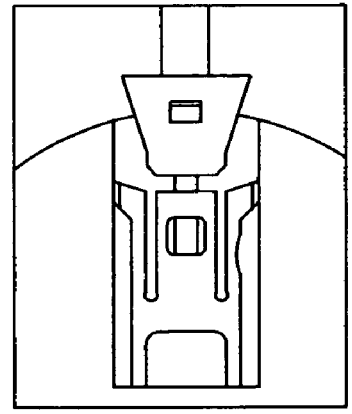
Figure 45C:
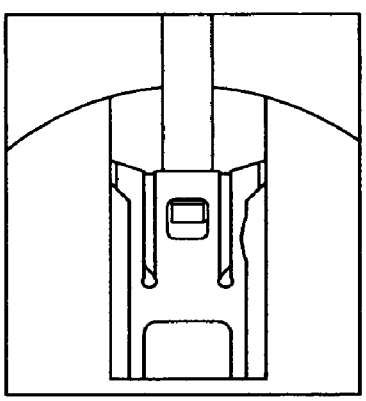
Figure 45D:
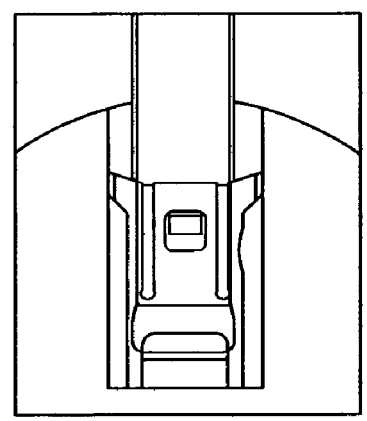
Figure 47A:
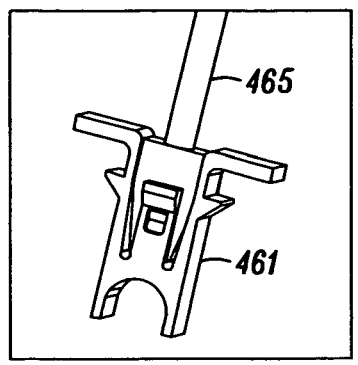
FIGS. 47A to 47F show side view of anchor delivery, inner wedge advancement and deployment of the substantially non-cylindrical tendon anchoring embodiment shown in FIGS. 46A to 46D.
Figure 47B:
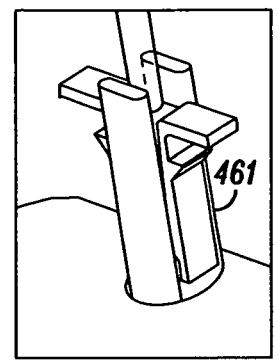
Figure 47C:
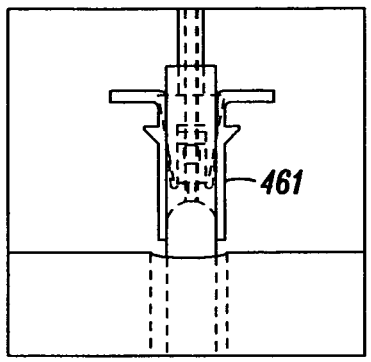
Figure 47D:
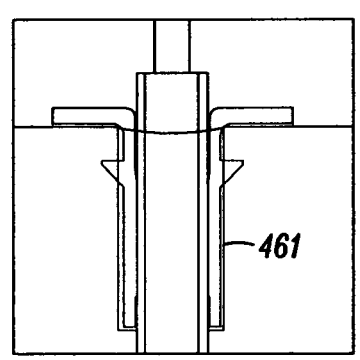
Figure 47E:
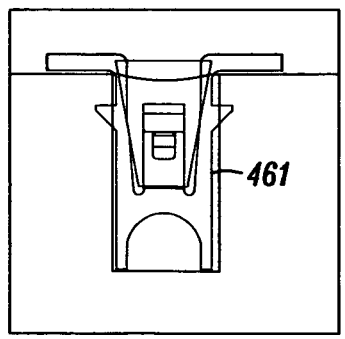
Figure 47F:
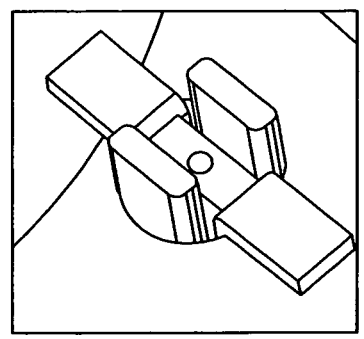
Figure 48A:
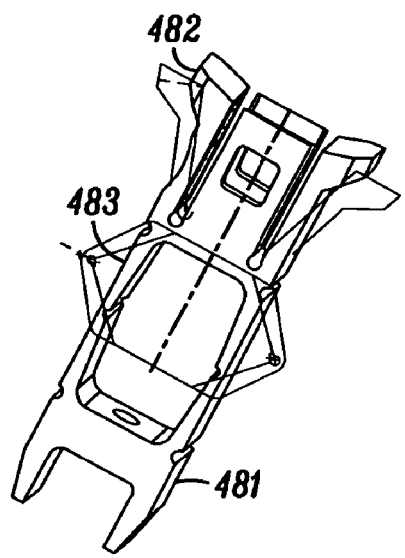
FIGS. 48A to 48D show isometric views, side view, and top view of a substantially non-cylindrical multiple component tendon anchor embodiment of the invention with two levels of expanding sections.
Figure 48B:
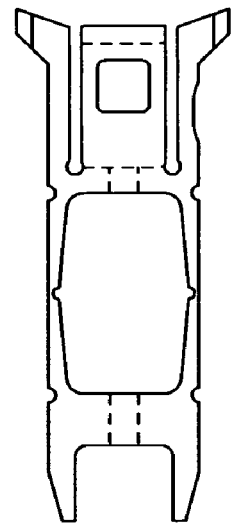
Figure 48C:
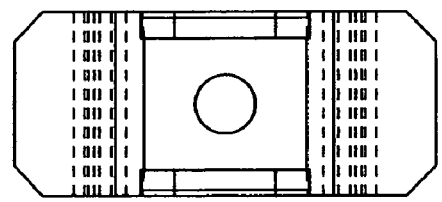
Figure 48D:
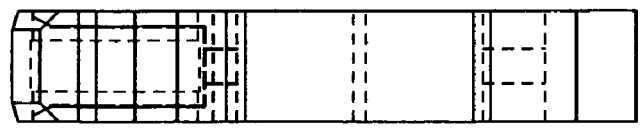

FIGS. 45A to 45C show side view of anchor delivery, inner wedge advancement and deployment of the substantially non-cylindrical tendon anchoring embodiment shown in FIGS. 42A to 42D. The mechanism for deployment of this embodiment, as well as the other exemplary embodiments shown in FIGS. 41-44 closely relate to the mechanism shown with respect to FIGS. 39 and 40.

FIGS. 46A to 46D show isometric views, side view, and top view of an exemplary substantially non-cylindrical, multiple component tendon anchor embodiment 461 according to the present invention. Exemplary uses for this embodiment include cortical bone shell and trabecular bone interface as an anchoring advantage. All elements of this embodiment 461 include those described in FIGS. 40-45. However, the variation described here include an expanded lateral flange 462, which is intended to abut the outer surface of the cortical bone at the bone hole surface, and a lower profile lateral flange 463 just distal to the expanded lateral flange 462, which is intended to abut the inner surface of the cortical bone surface. The gap between the two flanges 464 can vary between implant embodiments to include the range of cortical bone thicknesses expected at each implant site. Note that the lower profile flange 463 need not abut the inner surface of the cortical bone, but may act as described in previous embodiment wherein the arm extension is expanded into the bone surface, anchoring the implant into position. The basic premise of this design is to use the cortical bone cortex to provide additional fixation support.

FIGS. 47A to 47F show side view of anchor delivery, inner wedge advancement and deployment of the tendon anchoring embodiment 461 shown in FIGS. 46A to 46D. Such mode of delivery using a deployment device 465 and technique used is substantially similar to that described with respect to FIGS. 39 and 40.

FIGS. 48A to 48D show isometric views, side view, and top view of an exemplary substantially non-cylindrical, multiple component tendon anchor embodiment 481 of the invention with two levels of expanding sections. The proximal end 482 of the anchor implant is a similar embodiment to that described in FIGS. 40-47. An additional embodiment is included here with a mid-section 483 which is expandable upon deployment of the implant. Specifically, once the implant 481 is in position and as the wedge is advanced to expand the lateral arms, the center section 483 will collapse and expand outward. Additional facets can be added on the surface of the mid-section 483 to promote anchoring in the bone. The resulting implant structure 481 in this embodiment is intended to provide two levels of implant fixation in the bone hole.

Figure 49A:
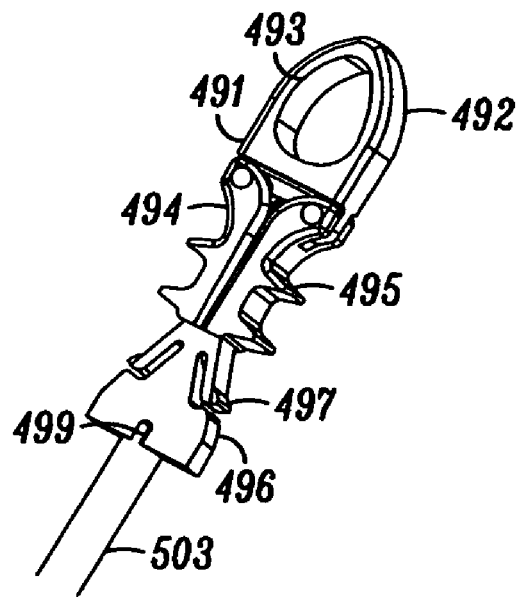
FIGS. 49A and 49B show perspective views of a tendon anchor embodiment according to the present invention with pivoting arms and a wedge deployment mechanism disengaged and engaged with the anchor.
Figure 49B:
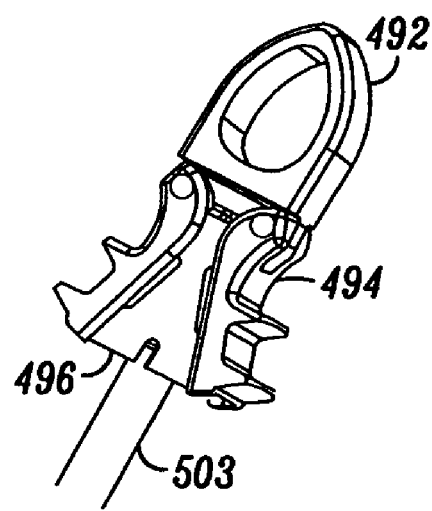

FIGS. 49A and 49B show another exemplary embodiment of the present invention as a multi-piece anchor unit 491. An anchor portion 492 has a tendon receiving portion 493 and a pair of pivoting arms 494. The pivoting arms 494 may include tabs 495 that assist in the securing of the anchor portion 492 within a bone hole. A separating wedge 496 is shaped to fit and separate the pair of pivoting arms 494 and can be made thicker or bulbous in the middle so that the tendons can be compressed more against the bone wall. Locking tabs 497 positioned on the exterior portion of the separating wedge 496 assist in the locking of the separating wedge 496 with mating tabs located inside of the pivoting arms 494.

Figure 50:
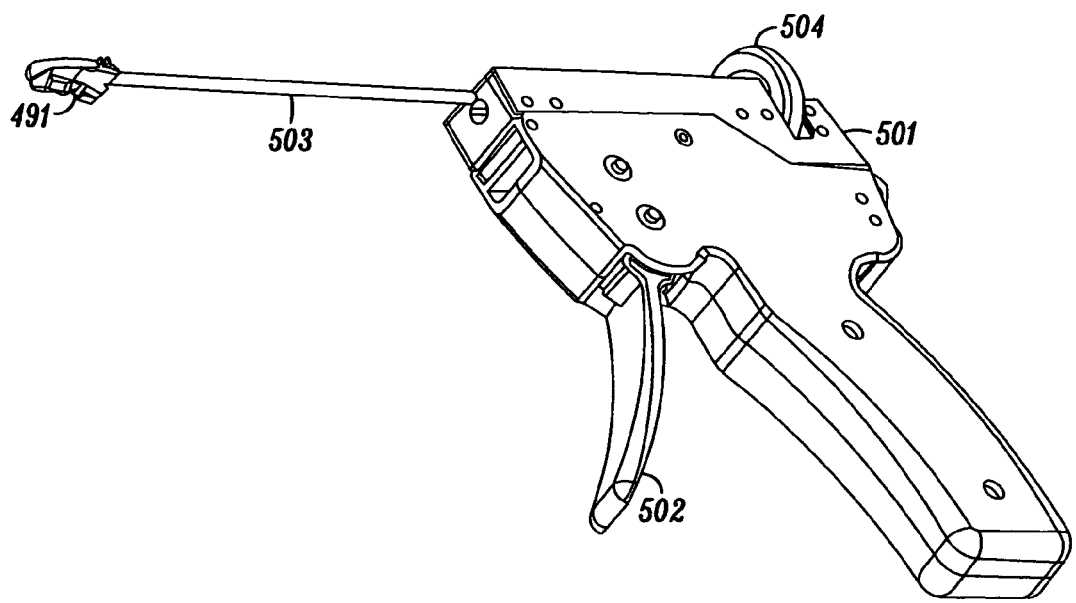
FIG. 50 shows an exemplary deployment mechanism used for the deployment of tendon anchor embodiment shown in FIGS. 49A and B.

A deployment device 501, as shown in FIG. 50, may be used to deploy the anchor unit 491 within a bone hole in a bone. The deployment device 501 includes a trigger 502 that is used to push the tube 503 into the separating wedge 496. In use, deployment is achieved by having a threaded rod screw into a threaded hole 499 in the body of the wedge 492, while the tube 503 pushes the wedge 496 into place by using the trigger 502, thus spreading the pivoting arms 494 outward and into the bone. Once the pivoting arms 494 are deployed into the bone and secured therein by tabs 495, the threaded rod is unscrewed via the wheel 504 at the back of the deployment device 501, releasing the anchor unit 491 from the deployment device 501.

Device Materials

Anchor and deployment instrument components can incorporate elastic properties or be deformable. As such, the anchor or deployment instrument components can be fabricated from various materials [e.g., shape memory alloys (e.g., nickel titanium (Nitinol)), shape memory polymers, polymers (e.g., PTFE, polyurethane, urethane, silicone, polyimide, polypropylene, Polylactic Acid, Polyglycolic Acid, or other thermoset or thermoplastic, or elastomeric materials), and metal or alloys (e.g., titanium, CoCrMo, stainless steel, etc)]. In some embodiments, the device anchor components can be resorbable, in other embodiments, the device components will have limited or no resorption characteristics. The anchor components described herein be made in part or solely of one material. Alternatively, the components of the anchors or deployment instruments can be composed of metal and/or polymer components fabricated into composite devices. For example, low surface area and thin metal or metal alloy components can be insert molded with a polymer (e.g., polypropylene) to produce a composite device.

Some embodiments may include parts that are resorbable and some that are not. Fabrication of these components can be performed using techniques familiar with manufacturing methods by those skilled in the art of metals, polymers, shape memory alloys, shape memory polymers, or composite materials. Sample techniques will include but are not limited to extrusion, casting, press-forging, rolling, or pressing methods for the fabrication of parts for the above materials.

In specific instances, the use of techniques related to modification of polymer chemistry to adjust the shape memory characteristics related to thermal conditions and elastic properties of the polymer will be utilized. With respect to shape memory metal materials, one having ordinary skill in the art will utilize the thermal characteristics of the specified composition to fabricate components with the geometry and features required for the device component. Proper thermal forming and quenching is required to process the material and is generally known to someone skilled in the art of using, processing, and fabricating components out of shape memory materials. In some embodiments several components may require parts using standard machining techniques typically known to someone skilled in the art of machining. For example, use of CNC, EDM, laser cutting, water jet cutting, polishing methods, and other machining techniques. Several embodiments may also require bonding or welding of components and include adhesives, laser welding, soldering, or other means of attachment.

Anchor components that include spikes or tabs can be fabricated from any stock materials typically known to those having ordinary skill in the art of medical device manufacturing. Attachment of other components to these embodiments can be performed by tying, welding, bonding, clamping, embedding, or use of other such means. In some embodiments, these anchors can be mechanically polished or electropolished to produce smooth surfaces.

Various embodiments of the clip components described can be coated with or encapsulated with a covering of a polymer material that can allow for the use of anti-proliferative, antibiotic, angiogenic, growth factors, anti-cancer, or other pharmacological substances that may provide a benefit related to inhibiting or promoting biological proliferation. These substances would be loaded into the encapsulating coatings and be allowed to elute into the surrounding matrix, tissues, or space that it sits. The time course of delivery can be tailored to the intended application by varying the polymer or the characteristics of the coating. Such coatings with pharmacological substances can act as anti-proliferative treatments or can aid in the healing response of the tissue being treated. Furthermore, these coatings can act to reduce the local coagulation or hyperplastic response near the anchor.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A material fixation system, comprising an implant which is placeable in a space defined by bone, said implant comprising:
a body having a distal end and a proximal end;
a first member on said body which is expandable outwardly to engage portions of the bone, said first member comprising a plurality of mating pieces, said mating pieces being free moving and slidable outwardly relative to one another; and a second member on said body which is distal to said first member;

said second member being movable in a proximal direction relative to said first member, wherein proximal movement of said second member actuates said first member to expand outwardly to engage the bone, thereby securing the implant in place within the space.

2. The material fixation system as recited in claim 1, wherein said second member is actuated by application of tension thereon.

3. The material fixation system as recited in claim 2, said second member comprising a surface for receiving soft tissue thereon which is to be anchored within said space, wherein tension may be applied to the soft tissue to thereby apply tension to said second member.

4. The material fixation system as recited in claim 3, wherein said second member comprises a distal tip about which soft tissue may be looped.

5. A material fixation system, comprising an implant which is placeable in a space defined by bone, said implant comprising:

a body having a longitudinal axis, a distal end, and a proximal end;

a first member on said body which is movably expandable outwardly, said first member having a substantially outermost contacting portion when said first member is expanded outwardly for contacting adjacent soft tissue or bone;

a second member on said body which is disposed axially from said first member and is also movably expandable outwardly, said second member having a substantially outermost contacting portion when said second member is expanded outwardly for contacting adjacent soft tissue or bone;

a distal end of said body comprising a space for receiving soft tissue therethrough, said space being defined by surfaces of said body which are oriented both generally parallel to said longitudinal axis and generally transverse to said longitudinal axis; and a wedge which is movable in a generally axial direction relative to said first and second members to deploy at least one of said first and second members wherein the substantially outermost contacting portion of the first member and the substantially outermost contacting portion of the second member are at axially different locations along said body.

6. The material fixation system as recited in claim 5, wherein said second member is disposed distally of said first member.

7. The material fixation system as recited in claim 5, wherein said second member is always proximal to said distal end.

8. The material fixation system as recited in claim 5, wherein said first member comprises an arm which is pivotable outwardly, said arm having a portion which is adapted to engage bone to anchor the body to the bone.

9. The material fixation system as recited in claim 8, wherein a distal end of the arm is attached to the body, and comprises the pivoting end, and a proximal end of the arm pivots outwardly and comprises the portion which is adapted to engage bone.

10. The material fixation system as recited in claim 8, wherein said first member comprises a plurality of said arms.

11. The material fixation system as recited in claim 5, wherein said second member comprises a mid-section which may be actuated to a collapsed orientation, wherein it is expanded outwardly.

12. A method of anchoring soft tissue to bone, comprising:

placing the soft tissue on an implant having a longitudinal axis extending from a distal end of the implant to a proximal end of the implant, and disposing the implant within a space at a desired location within a patient's body;

deploying a first member on said implant outwardly to engage adjacent bone with a substantially outermost contacting portion of the first member at a first axial location; and deploying a second member, disposed on said implant in axially spaced relationship from the first member, outwardly to engage adjacent bone with a substantially outermost contacting portion of the second member at a second axial location which is different than said first axial location;

wherein the outward deployment of one of said first and second members compresses the soft tissue between said one of said first and second members and adjacent bone.

13. The method as recited in claim 12, wherein each of said deploying steps are performed by moving a deployment device in a generally axial direction.

14. The method as recited in claim 12, wherein said second member is disposed distally of said first member.

15. The method as recited in claim 12, wherein said adjacent material comprises bone.

16. The method as recited in claim 12, wherein the soft tissue comprises a tendon.

17. The method as recited in claim 12, wherein the soft tissue comprises a graft.

18. The method as recited in claim 12, wherein the first member comprises a hinged arm, and a wedge is moved axially to pivot the hinged arm outwardly.

\* \* \* \* \*

UNITED STATES PATENT AND TRADEMARK OFFICE
CERTIFICATE OF CORRECTION

PATENT NO. : 7,651,528 B2  Page 1 of 1
APPLICATION NO. : 11/281566
DATED : January 26, 2010
INVENTOR(S) : Montgomery et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 263 days.

Signed and Sealed this

Twenty-third Day of November, 2010

David J. Kappos
*Director of the United States Patent and Trademark Office*